United States Patent
Odell et al.

(10) Patent No.: US 7,060,813 B1
(45) Date of Patent: Jun. 13, 2006

(54) PLANT RNA-DIRECTED RNA POLYMERASE PROTEINS

(75) Inventors: Joan T. Odell, Unionville, PA (US); Rebecca E. Cahoon, Wilmington, DE (US); Jimei Wang, Johnston, IA (US); Gan-Yuan Zhong, Urbandale, IA (US); Karlene H. Butler, Newark, DE (US)

(73) Assignees: E. I. du Pont de Nemours and Company, Wilmington, DE (US); Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 09/958,109

(22) PCT Filed: Apr. 6, 2000

(86) PCT No.: PCT/US00/09105

§ 371 (c)(1),
(2), (4) Date: Oct. 2, 2001

(87) PCT Pub. No.: WO00/60097

PCT Pub. Date: Oct. 12, 2000

Related U.S. Application Data

(60) Provisional application No. 60/128,094, filed on Apr. 7, 1999.

(51) Int. Cl.
  *C12N 15/29*  (2006.01)
  *C12N 15/52*  (2006.01)
  *C12N 15/82*  (2006.01)
  *A01H 5/00*  (2006.01)
  *A01H 5/10*  (2006.01)

(52) U.S. Cl. .................. 536/23.6; 536/23.1; 536/23.2; 435/320.1; 435/419; 800/278; 800/287; 800/298

(58) Field of Classification Search .............. 536/23.1, 536/23.2, 23.6; 435/182, 320, 320.1, 419; 800/278, 28, 287, 298
See application file for complete search history.

(56) References Cited

OTHER PUBLICATIONS

Schiebel W. et al. The Plant Cell, Dec. 1998, vol. 10, pp. 2087-2101.*
Winfried Schiebel et al., Plant Cell, vol. 10:2087-2101, Dec. 1998, Isolation of an RNA-Directed RNA Polymerase-Specific CDNA Clone From Tomato.
Z. A. Khan et al., PNAS, vol. 83:2383-2386, Apr. 1986, RNA-Directed RNA Polymerases From Healthy and From Virus-Infected Cucumber.
Michael Wassenegger et al., Plant Mol. Biology, vol. 37:349-362, 1998, A Model for RNA-Mediated Gene Silencing in Higher Plants.
EMBL Sequence Database Library Accession No.: AQ861550, Nov. 9, 1999, R. A. Wing et al., A BAC End Sequencing Framework to Sequence the Rice Genome.
Beatriz Xoconostle-Cazares et al., Science, vol. 283:94-98, 1999, Plant Paralog to Viral Movement Protein That Potentiates Transport of MRNA Into the Phloem.
National Center for Biotechnology Information General Identifier No. 3600048, Sep. 15, 1998, Washington University Genome Sequencing Center, the *A. thaliana* Genome Sequencing Project.
National Center for Biotechnology Information General Identifier No. 3687225, Apr. 5, 2000, X. Lin et al., Sequence and Analysis of Chromosome 2 of the Plant *Arabidopsis thaliana*.
Xiaoying Lin et al., Nature, vol. 402:761-768, 1999, Sequence and Analysis of Chromosome 2 of the Plant *Arabidopsis thaliana*.
National Center for Biotechnology Information General Identifier No. 6553930, Oct. 12, 2000, X. Lin et al., *Arabidopsis thaliana* Chromosome 1 BAC T1G12 Genomic Sequence.
National Center for Biotechnology Information General Identifier No. 4138282, Jan. 7, 1999, M. Wassenegger.
Tamas Dalmay et al., An RNA-Dependent RNA Polymerase Gene in *Arabidopsis* is Required for Posttranscriptional Gene Silencing Mediated by a Transgene But Not by a Virus, Cell, vol. 101:543-553, 2000.
Philippe Mourrain et al., *Arabidopsis* SGS2 and SGS3 Genes Are Required for Posttranscriptional Gene Silencing and Natural Virus Resistance, Cell, vol. 101:533-542, 2000.

* cited by examiner

*Primary Examiner*—Russell P. Kallis
(74) *Attorney, Agent, or Firm*—E. I. du Pont de Nemours and Company

(57) ABSTRACT

This invention relates to an isolated nucleic acid fragment encoding a RNA-directed RNA polymerase. The invention also relates to the construction of a chimeric gene encoding all or a substantial portion of the RNA-directed RNA polymerase, in sense or antisense orientation, wherein expression of the chimeric gene results in production of altered levels of the RNA-directed RNA polymerase in a transformed host cell.

9 Claims, No Drawings

SEQUENCE LISTING

<160> NUMBER OF SEQ ID NOS: 20

<210> SEQ ID NO 1
<211> LENGTH: 474
<212> TYPE: DNA
<213> ORGANISM: Zea mays
<220> FEATURE:
<221> NAME/KEY: unsure
<222> LOCATION: (294)
<223> OTHER INFORMATION: n=a,c,g or t

<400> SEQUENCE: 1

```
cagatcctac aggaacgctg aaaccaaatg aagtttgtgt gatacttgac agcggacaat      60
actctggaga tgttcttgtg tttaaacatc ctgggctaca ttttggcgat atacatatct     120
taactgcaag gcaaattgat ggactagaga agaattttat tggatattca aaaaatgcaa    180
tactttttcc tacttctgga caaagatcat tggctgatga gatggccaat agtgattttg    240
atggtgacga gttctgggtc tcaagaaaca atatgttaca caaaaggttt agcncctgac    300
tgttggttag cacatatgga ccgattatta acagaaggag tcgatcaaga tgagaagaag    360
tcaatcgtgg aaaacatgat taaattagtt gacctttatt atgcggctct ggatgggcac    420
aaggtacatg ttgatcccca tctgagagta aaagcatatc cacacttcaa tggg           474
```

<210> SEQ ID NO 2
<211> LENGTH: 157
<212> TYPE: PRT
<213> ORGANISM: Zea mays

<400> SEQUENCE: 2

```
Asp Pro Thr Gly Thr Leu Lys Pro Asn Glu Val Cys Val Ile Leu Asp
  1               5                  10                  15

Ser Gly Gln Tyr Ser Gly Asp Val Leu Val Phe Lys His Pro Gly Leu
             20                  25                  30

His Phe Gly Asp Ile His Ile Leu Thr Ala Arg Gln Ile Asp Gly Leu
         35                  40                  45

Glu Lys Asn Phe Ile Gly Tyr Ser Lys Asn Ala Ile Leu Phe Pro Thr
     50                  55                  60

Ser Gly Gln Arg Ser Leu Ala Asp Glu Met Ala Asn Ser Asp Phe Asp
 65                  70                  75                  80

Gly Asp Glu Phe Trp Val Ser Arg Asn Asn Met Leu His Lys Gly Leu
                 85                  90                  95

Ala Pro Asp Cys Trp Leu Ala His Met Asp Arg Leu Leu Thr Glu Gly
            100                 105                 110

Val Asp Gln Asp Glu Lys Lys Ser Ile Val Glu Asn Met Ile Lys Leu
        115                 120                 125

Val Asp Leu Tyr Tyr Ala Ala Leu Asp Gly His Lys Val His Val Asp
    130                 135                 140

Pro His Leu Arg Val Lys Ala Tyr Pro His Phe Asn Gly
145                 150                 155
```

<210> SEQ ID NO 3
<211> LENGTH: 1281
<212> TYPE: DNA
<213> ORGANISM: Zea mays
<220> FEATURE:
<221> NAME/KEY: unsure
<222> LOCATION: (16)..(17)
<223> OTHER INFORMATION: n=a,c,g or t

```
<220> FEATURE:
<221> NAME/KEY: unsure
<222> LOCATION: (403)
<223> OTHER INFORMATION: n=a,c,g or t

<400> SEQUENCE: 3
ggcacgaggt ttacgnncat ccaggcaaac atttgaagtc tcatcatatg atgtagaagt      60
aattccagat attgaagtca caactgatgg cactaaatac atattttcag atggtatcgg     120
gaagatttct actagatttg ccagacaagt cgccaaatta attggcttag acccagctca     180
tcctccttct gcttttcaaa taaggtatgg gggctataaa ggagtcatca ctattgaccc     240
tacatccttt ttcaatcttt ctctgcgacc tagtatgaag aagtttgaat cgaagagcac     300
tatgctgaac attacaaatt ggagtaagtc tcagccatgt tatgtgaacc gtgaaattat     360
ctctcttctt tcaacattgg ggataaagga tgaagtattt gantcgatgc aacaagatga     420
catgcacgaa tcagatggaa tgctaacaaa taaagaagct gctttgtctg tcctagggaa     480
aattggtggc ggtgatacca agacggcagc tgatatgctt cttcaaggct atgaaccaag     540
ttcagagcct tacctattaa tgattcttaa agcccatcgg gctaataggc tgaccgacat     600
aagaactcgg tgtaagattc atgtccagaa aggccgtgtt cttattggtt gtttggatga     660
aacttgcaaa ttagagtatg gccaagttta catcagaatt acaaagaatc gcaaggagca     720
gaagtacagt gaacagccgt tcttttgcaa cgatgatggc aaaacagctg taattgtcgg     780
aaaagttgca atcacaaaaa acccttgtct ccatcctggt gatgtcagag tacttgaagc     840
tgtatatgac cctggattgg atgctagggg tcttattgat tgtgttgtat ttcctcagag     900
aggggaaagg cctcatccga atgaatgctc cggggcgat ttggatggcg acctcttctt     960
tattacttgg gatgacaaac tgattccgga aaggttgat gcacctatgg actacactgc    1020
aacgaggcca cgcataatgg accatgctgt tacacttgag gaaattcaga agcacttcgt    1080
cagttacatg ataaacgata ccctcggtgc catctccacc gcccacttga tccacgcaga    1140
ccgtgatccg ctgaaagctc gcagccccga gtgcgtccag ctggccgctc tgcactccat    1200
gggggtcgac ttcgccaaga cgggagctca gcccaagatt ccccttggcg cctgaggccc    1260
cgggagtttc ccggacttca t                                              1281

<210> SEQ ID NO 4
<211> LENGTH: 417
<212> TYPE: PRT
<213> ORGANISM: Zea mays
<220> FEATURE:
<221> NAME/KEY: UNSURE
<222> LOCATION: (6)
<223> OTHER INFORMATION: Xaa = ANY AMINO ACID
<220> FEATURE:
<221> NAME/KEY: UNSURE
<222> LOCATION: (134)
<223> OTHER INFORMATION: Xaa = ANY AMINO ACID

<400> SEQUENCE: 4

Ala Arg Gly Leu Arg Xaa Ser Arg Gln Thr Phe Glu Val Ser Tyr
  1               5                  10                  15

Asp Val Glu Val Ile Pro Asp Ile Glu Val Thr Thr Asp Gly Thr Lys
                 20                  25                  30

Tyr Ile Phe Ser Asp Gly Ile Gly Lys Ile Ser Thr Arg Phe Ala Arg
             35                  40                  45

Gln Val Ala Lys Leu Ile Gly Leu Asp Pro Ala His Pro Pro Ser Ala
         50                  55                  60
```

```
Phe Gln Ile Arg Tyr Gly Gly Tyr Lys Gly Val Ile Thr Ile Asp Pro
 65                  70                  75                  80

Thr Ser Phe Phe Asn Leu Ser Leu Arg Pro Ser Met Lys Lys Phe Glu
                 85                  90                  95

Ser Lys Ser Thr Met Leu Asn Ile Thr Asn Trp Ser Lys Ser Gln Pro
            100                 105                 110

Cys Tyr Val Asn Arg Glu Ile Ile Ser Leu Leu Ser Thr Leu Gly Ile
            115                 120                 125

Lys Asp Glu Val Phe Xaa Ser Met Gln Gln Asp Asp Met His Glu Ser
130                 135                 140

Asp Gly Met Leu Thr Asn Lys Glu Ala Ala Leu Ser Val Leu Gly Lys
145                 150                 155                 160

Ile Gly Gly Gly Asp Thr Lys Thr Ala Ala Asp Met Leu Leu Gln Gly
                165                 170                 175

Tyr Glu Pro Ser Ser Glu Pro Tyr Leu Leu Met Ile Leu Lys Ala His
            180                 185                 190

Arg Ala Asn Arg Leu Thr Asp Ile Arg Thr Arg Cys Lys Ile His Val
            195                 200                 205

Gln Lys Gly Arg Val Leu Ile Gly Cys Leu Asp Glu Thr Cys Lys Leu
210                 215                 220

Glu Tyr Gly Gln Val Tyr Ile Arg Ile Thr Lys Asn Arg Lys Glu Gln
225                 230                 235                 240

Lys Tyr Ser Glu Gln Pro Phe Phe Cys Asn Asp Asp Gly Lys Thr Ala
                245                 250                 255

Val Ile Val Gly Lys Val Ala Ile Thr Lys Asn Pro Cys Leu His Pro
            260                 265                 270

Gly Asp Val Arg Val Leu Glu Ala Val Tyr Asp Pro Gly Leu Asp Ala
            275                 280                 285

Arg Gly Leu Ile Asp Cys Val Val Phe Pro Gln Arg Gly Glu Arg Pro
290                 295                 300

His Pro Asn Glu Cys Ser Gly Gly Asp Leu Asp Gly Asp Leu Phe Phe
305                 310                 315                 320

Ile Thr Trp Asp Asp Lys Leu Ile Pro Glu Lys Val Asp Ala Pro Met
                325                 330                 335

Asp Tyr Thr Ala Thr Arg Pro Arg Ile Met Asp His Ala Val Thr Leu
            340                 345                 350

Glu Glu Ile Gln Lys His Phe Val Ser Tyr Met Ile Asn Asp Thr Leu
            355                 360                 365

Gly Ala Ile Ser Thr Ala His Leu Ile His Ala Asp Arg Asp Pro Leu
370                 375                 380

Lys Ala Arg Ser Pro Glu Cys Val Gln Leu Ala Ala Leu His Ser Met
385                 390                 395                 400

Gly Val Asp Phe Ala Lys Thr Gly Ala Gln Pro Lys Ile Pro Leu Gly
                405                 410                 415

Ala

<210> SEQ ID NO 5
<211> LENGTH: 3737
<212> TYPE: DNA
<213> ORGANISM: Zea mays

<400> SEQUENCE: 5
tcgcagtccg cagccataga aaccatctga ctcccgtcgg cgagccgcga gaggcgcaac        60
agaagttgtg atatgcacca tggtttggag aactattcag gtccaaggtt ttgctctaac       120
```

```
tgacagtgcc gaatctgtca aattgttttt ggagcgaatt gctggtgctg gaaccatctg      180
tgctctcaag ctcaggcatc aaggaacatc tctgccaaac tcaagggcat tgctatagt       240
tcagttccag tcacaggaaa gtgcttcatt ggtagagaat gcggctcaaa gacaggttct      300
caagattgga cggttttatc tgagaaccag acctgcagac cgggacattg ttccaagacc      360
aaggattcca atgttttctc tagaggacat tgtgctgcat ttgggatgct tggttaagga      420
aaatatccta tctgctcttt ttagagcaag taatgtttcg gttcaatttg gatttgatat      480
gaaaaagatc tacttctacc tctcctacaa ttttactaaa tttaaacttg aactttctta      540
cgaaagtata tgggagatgc agcttcaccg tccacctgct tataggtcac ggacacagtt      600
cctttttgatt caggttcagg cagctcctaa aatttataaa ctgctcccag gccgtccagg     660
tcttatgttt gaggatcctt tcttcaactg gtttagggat gacacagatg aacaatggac      720
caggacaatt gatttactc catcagctag catcgggcaa tcatctattt tatgtctgga       780
ggtgccacaa cagtgtgagc ttccaagaat tggcgactac tttgtttact ataaagagca      840
gaatcttgac tttgaatgtc ggaatgggta ttcatattcc tgtggtagca accttgtacc      900
aattgtgaaa tctcctgatt acatagaggt cccttatgag atactcttca aaatcaacca      960
tttggttcag aatgggacac tcagtgggcc aacagttgat catagtttct tccgtcatgt     1020
tagcccaaaa tttgaaccta ttgatcatat aaaacgagca cttttaaaga tgacatattt     1080
gaaaagcacc tgcttgaacc caacagattg gttatctgtg caatactcca gaatacggaa     1140
atcacgccat gcatcacaaa agttatctaa tatatctctg gatgatggct tggtctatgt     1200
ccacagggtg caagttaccc ctgctaaagt gtatttttat ggacctgaga taaatgtctc     1260
caatcgcgtt gtgcggcatt tctctgcaga catagataac ttccttcgga tttcatttgt     1320
tgatgaagac tgtgagaagc tccgttcagc tgatttgtca cctcgatcta cttctggaaa     1380
tgatgcaagg agaactgctc tgtataatag agttttgtca gtcctttcaa atggcatcaa     1440
tattggtgac aagcactttg agtttcttgc cttttcttca agtcagcttc gagataactc     1500
tgcatggatg tttgcttctc ggcagggatt gactgcgagc gacataagga agtggatggg     1560
ggactttcga gatatcagaa atgtggcaaa gtatgctgca atacttgggc aatctttcag     1620
ttcctcaaca gaaactttaa aagtacacaa atctgaggtg gaacgaattc ctgatattac     1680
aaatggcaca agtacatat tctctgatgg agttggaaag atctcagcta attttgcagt      1740
ggaggtggct atgaagtgca aattgaaacg ctttgctcct tctgtttttc agataaggta     1800
tggcggttac aaaggtgttg tcgctgtaga tacaagatca aatcataagc tttctttgag     1860
aaaaagcatg tcaaagttcc agtcagaaaa tatcactctt gatgtccttg catacagcaa     1920
gtaccaacca tgcttcctga atcggcagtt gattactctt ctctcaacac ttggggttag     1980
cgataatgtc tttgagctaa agcagaagga agccttaagg cagttgaaca gaatggtaac     2040
tgaaccacag gctgctcgtg aagcagttga acttatgccc atgggagagg taaccaatgt     2100
agttaaagaa ttgttgtcat gtggctacca gcctgatcat gagccatatc tttccatgct     2160
gctacaaact tttagagcat ccaagcttct agagttgaaa acaaagtcaa ggatattcat     2220
cacacagggg cgagcaatga tgggttgcct ggatgaaacc tgcacactta agtacggcca     2280
ggtattcgtc caagcttctt acagtgcaga tgaccatcgc aaggtcgttg taactggaaa     2340
agtagttgtc gccaaaaatc cttgtctcca ccctggtgac atacgggttc tccaggctgt     2400
tgatgttcct gctctgcacc acttgtttga ctgtgttgtc tttccacagc agggaccaag     2460
```

```
gccgcacct  aatgagtgtt  cagggagtga  tcttgatggg  gacatatatt  ttgtttcttg   2520
ggatccacat  cttattccaa  gtcgtttggt  ggatcctatg  gactatactc  cagcttcagc   2580
agaaacatta  gaccatgatg  tcactattga  ggagatacag  gagtacttca  caaactacat   2640
agttaatgag  agtcttggga  ttatcgccaa  tgcgcatgtg  gtctttacag  atcaggaacg   2700
tatgaaagct  gagagtccac  cgtgcgttca  actggccaag  ctcttctcta  tagctgtcga   2760
tttcccaaag  actggagtgc  cggctctgat  tccacatgag  ctacatgtca  aggagtatcc   2820
tgacttcatg  gagaaactcg  acaaagtcac  ctatgaatca  aagggtgtga  tcgggaagct   2880
ctatagggaa  ataagaagc   cacaccaca   cataaagcac  ttcacgaggg  aagtggcaag   2940
gcggtcttat  gacaccgatt  tgattgttga  tggctatgaa  gattacatta  ctgaggctat   3000
agagttcaag  gaagagtacg  atttcaggct  gggtaatctt  atggaccact  atggcataaa   3060
aagtgaagct  gagataataa  gtggatgtat  tctaaagatg  gcaagaatt   tcaccaagag   3120 tagtgatgct  gatgcaatta  aatggcggt   gagatctttg  aggaaagaag  ctaggtcgtg   3180
gttcaatgag  atgagcacag  gagaggatgg  ccaagatgcc  atggaggcca  aggcctctgc   3240
ttggtaccat  gttacttatc  atcagcagta  ctggggcagc  tacaatgaag  ggtatgatcg   3300
gccgcatctt  attagcttcc  catggtgcgt  atatgacaag  cttgtggcca  tcaagcaggg   3360
gaggaatctc  ctcacgcaga  tggatcgaaa  cttgaggttc  cgttgagcat  tgccagcagg   3420
tttgctcctg  tacatatccc  tgatcgtttg  caatcagcac  tgccagcaag  tgtgcatgaa   3480
cgatctgatg  aattaagacg  ggcaaactgc  cgcaagctga  cgctctggcg  tacgtgcgtc   3540
ttgaaacttt  cggatgctgc  cgtctagcta  aatgcatctt  ccttgatttc  cactgggacc   3600
ttgagtttga  agtgtgtaaa  tatatgctgc  ttatgatgtt  tttagtattg  gacctctatc   3660
aactgccttt  ctagttagta  acaatggttg  gcagtccaaa  aaaaaaaaaa  aaaaaaaaaa   3720
aaaaaaaaaa  aaaaaaa                                                     3737
```

<210> SEQ ID NO 6
<211> LENGTH: 1108
<212> TYPE: PRT
<213> ORGANISM: Zea mays

<400> SEQUENCE: 6

```
Met Val Gly Arg Thr Ile Gln Val Gln Gly Phe Ala Leu Thr Asp Ser
 1               5                  10                  15

Ala Glu Ser Val Lys Leu Phe Leu Glu Arg Ile Ala Gly Ala Gly Thr
            20                  25                  30

Ile Cys Ala Leu Lys Leu Arg His Pro Arg Asn Ile Ser Ala Asn Ser
        35                  40                  45

Arg Ala Phe Ala Ile Val Gln Phe Gln Ser Gln Glu Ser Ala Ser Leu
    50                  55                  60

Val Glu Asn Ala Ala Gln Arg Gln Val Leu Lys Ile Gly Arg Phe Tyr
65                  70                  75                  80

Leu Arg Thr Arg Pro Ala Asp Arg Asp Ile Val Pro Arg Pro Arg Ile
                85                  90                  95

Pro Met Phe Ser Leu Glu Asp Ile Val Leu His Leu Gly Cys Leu Val
            100                 105                 110

Lys Glu Asn Ile Leu Ser Ala Leu Phe Arg Ala Ser Asn Val Ser Val
        115                 120                 125

Gln Phe Gly Phe Asp Met Lys Lys Ile Tyr Phe Leu Ser Tyr Asn
    130                 135                 140
```

```
Phe Thr Lys Phe Lys Leu Glu Leu Ser Tyr Glu Ser Ile Trp Glu Met
145                 150                 155                 160

Gln Leu His Arg Pro Pro Ala Tyr Arg Ser Arg Thr Gln Phe Leu Leu
            165                 170                 175

Ile Gln Val Gln Ala Ala Pro Lys Ile Tyr Lys Leu Leu Pro Gly Arg
            180                 185                 190

Pro Gly Leu Met Phe Glu Asp Pro Phe Phe Asn Trp Phe Arg Asp Asp
        195                 200                 205

Thr Asp Glu Gln Trp Thr Arg Thr Ile Asp Phe Thr Pro Ser Ala Ser
        210                 215                 220

Ile Gly Gln Ser Ser Ile Leu Cys Leu Glu Val Pro Gln Gln Cys Glu
225                 230                 235                 240

Leu Pro Arg Ile Gly Asp Tyr Phe Val Tyr Tyr Lys Glu Gln Asn Leu
            245                 250                 255

Asp Phe Glu Cys Arg Asn Gly Tyr Ser Tyr Ser Cys Gly Ser Asn Leu
            260                 265                 270

Val Pro Ile Val Lys Ser Pro Asp Tyr Ile Glu Val Pro Tyr Glu Ile
        275                 280                 285

Leu Phe Lys Ile Asn His Leu Val Gln Asn Gly Thr Leu Ser Gly Pro
        290                 295                 300

Thr Val Asp His Ser Phe Phe Arg His Val Ser Pro Lys Phe Glu Pro
305                 310                 315                 320

Ile Asp His Ile Lys Arg Ala Leu Leu Lys Met Thr Tyr Leu Lys Ser
            325                 330                 335

Thr Cys Leu Asn Pro Thr Asp Trp Leu Ser Val Gln Tyr Ser Arg Ile
            340                 345                 350

Arg Lys Ser Arg His Ala Ser Gln Lys Leu Ser Asn Ile Ser Leu Asp
            355                 360                 365

Asp Gly Leu Val Tyr Val His Arg Val Gln Val Thr Pro Ala Lys Val
        370                 375                 380

Tyr Phe Tyr Gly Pro Glu Ile Asn Val Ser Asn Arg Val Val Arg His
385                 390                 395                 400

Phe Ser Ala Asp Ile Asp Asn Phe Leu Arg Ile Ser Phe Val Asp Glu
            405                 410                 415

Asp Cys Glu Lys Leu Arg Ser Ala Asp Leu Ser Pro Arg Ser Thr Ser
            420                 425                 430

Gly Asn Asp Ala Arg Arg Thr Ala Leu Tyr Asn Arg Val Leu Ser Val
        435                 440                 445

Leu Ser Asn Gly Ile Asn Ile Gly Asp Lys His Phe Glu Phe Leu Ala
450                 455                 460

Phe Ser Ser Gln Leu Arg Asp Asn Ser Ala Trp Met Phe Ala Ser
465                 470                 475                 480

Arg Gln Gly Leu Thr Ala Ser Asp Ile Arg Lys Trp Met Gly Asp Phe
            485                 490                 495

Arg Asp Ile Arg Asn Val Ala Lys Tyr Ala Ala Ile Leu Gly Gln Ser
            500                 505                 510

Phe Ser Ser Thr Glu Thr Leu Lys Val His Lys Ser Glu Val Glu
            515                 520                 525

Arg Ile Pro Asp Ile Thr Asn Gly Thr Lys Tyr Ile Phe Ser Asp Gly
            530                 535                 540

Val Gly Lys Ile Ser Ala Asn Phe Ala Val Glu Val Ala Met Lys Cys
545                 550                 555                 560

Lys Leu Lys Arg Phe Ala Pro Ser Val Phe Gln Ile Arg Tyr Gly Gly
```

-continued

|   |   |   |   |   |   |   |   |   |   |   |   |
|---|---|---|---|---|---|---|---|---|---|---|---|
| | | | | 565 | | | 570 | | | 575 | |
| Tyr | Lys | Gly | Val | Val | Ala | Val | Asp | Thr | Arg | Ser | Asn | His | Lys | Leu | Ser |

Tyr Lys Gly Val Val Ala Val Asp Thr Arg Ser Asn His Lys Leu Ser
              580                     585                 590

Leu Arg Lys Ser Met Ser Lys Phe Gln Ser Glu Asn Ile Thr Leu Asp
         595                     600                 605

Val Leu Ala Tyr Ser Lys Tyr Gln Pro Cys Phe Leu Asn Arg Gln Leu
     610                 615                 620

Ile Thr Leu Leu Ser Thr Leu Gly Val Ser Asp Asn Val Phe Glu Leu
625                 630                 635                 640

Lys Gln Lys Glu Ala Leu Arg Gln Leu Asn Arg Met Val Thr Glu Pro
                 645                 650                 655

Gln Ala Ala Arg Glu Ala Val Glu Leu Met Pro Met Gly Glu Val Thr
             660                 665                 670

Asn Val Val Lys Glu Leu Leu Ser Cys Gly Tyr Gln Pro Asp His Glu
         675                 680                 685

Pro Tyr Leu Ser Met Leu Leu Gln Thr Phe Arg Ala Ser Lys Leu Leu
     690                 695                 700

Glu Leu Lys Thr Lys Ser Arg Ile Phe Ile Thr Gln Gly Arg Ala Met
705                 710                 715                 720

Met Gly Cys Leu Asp Glu Thr Cys Thr Leu Lys Tyr Gly Gln Val Phe
                 725                 730                 735

Val Gln Ala Ser Tyr Ser Ala Asp Asp His Arg Lys Val Val Val Thr
             740                 745                 750

Gly Lys Val Val Ala Lys Asn Pro Cys Leu His Pro Gly Asp Ile
         755                 760                 765

Arg Val Leu Gln Ala Val Asp Val Pro Ala Leu His His Leu Phe Asp
     770                 775                 780

Cys Val Val Phe Pro Gln Gln Gly Pro Arg Pro His Pro Asn Glu Cys
785                 790                 795                 800

Ser Gly Ser Asp Leu Asp Gly Asp Ile Tyr Phe Val Ser Trp Asp Pro
                 805                 810                 815

His Leu Ile Pro Ser Arg Leu Val Asp Pro Met Asp Tyr Thr Pro Ala
             820                 825                 830

Ser Ala Glu Thr Leu Asp His Asp Val Thr Ile Glu Glu Ile Gln Glu
         835                 840                 845

Tyr Phe Thr Asn Tyr Ile Val Asn Glu Ser Leu Gly Ile Ile Ala Asn
     850                 855                 860

Ala His Val Val Phe Thr Asp Gln Glu Arg Met Lys Ala Glu Ser Pro
865                 870                 875                 880

Pro Cys Val Gln Leu Ala Lys Leu Phe Ser Ile Ala Val Asp Phe Pro
                 885                 890                 895

Lys Thr Gly Val Pro Ala Leu Ile Pro His Glu Leu His Val Lys Glu
             900                 905                 910

Tyr Pro Asp Phe Met Glu Lys Leu Asp Lys Val Thr Tyr Glu Ser Lys
         915                 920                 925

Gly Val Ile Gly Lys Leu Tyr Arg Glu Ile Lys Lys His Thr Pro His
     930                 935                 940

Ile Lys His Phe Thr Arg Glu Val Ala Arg Arg Ser Tyr Asp Thr Asp
945                 950                 955                 960

Leu Ile Val Asp Gly Tyr Glu Asp Tyr Ile Thr Glu Ala Ile Glu Phe
                 965                 970                 975

Lys Glu Glu Tyr Asp Phe Arg Leu Gly Asn Leu Met Asp His Tyr Gly
             980                 985                 990

```
Ile Lys Ser Glu Ala Glu Ile Ile Ser Gly Cys Ile Leu Lys Met Ala
        995                 1000                1005

Lys Asn Phe Thr Lys Ser Ser Asp Ala Asp Ala Ile Arg Met Ala Val
    1010                1015                1020

Arg Ser Leu Arg Lys Glu Ala Arg Ser Trp Phe Asn Glu Met Ser Thr
1025                1030                1035                1040

Gly Glu Asp Gly Gln Asp Ala Met Glu Ala Lys Ala Ser Ala Trp Tyr
                1045                1050                1055

His Val Thr Tyr His Gln Gln Tyr Trp Gly Ser Tyr Asn Glu Gly Tyr
            1060                1065                1070

Asp Arg Pro His Leu Ile Ser Phe Pro Trp Cys Val Tyr Asp Lys Leu
        1075                1080                1085

Val Ala Ile Lys Gln Gly Arg Asn Leu Leu Thr Gln Met Asp Arg Asn
    1090                1095                1100

Leu Arg Phe Arg
1105

<210> SEQ ID NO 7
<211> LENGTH: 3901
<212> TYPE: DNA
<213> ORGANISM: Zea mays
<220> FEATURE:
<221> NAME/KEY: unsure
<222> LOCATION: (503)..(504)
<223> OTHER INFORMATION: n=a,c,g or t
<220> FEATURE:
<221> NAME/KEY: unsure
<222> LOCATION: (595)
<223> OTHER INFORMATION: n=a,c,g or t

<400> SEQUENCE: 7
gcacgaggct cctccagcat ccacccaacg gatccgcggc aaccgaccac ccatgggatc        60
gctccggggc gcggcagcct cctccgcggc gccgcgcgcg ggcgacctgg tgaccacgca       120
ggttagcctt ggtggatttg atgccaccgt caaggcgctc gatctcgccg acttcctcga       180
gttgaatgcg ggctcggtct ggcgctgccg ccttaagacc tcctggactc cgccggacgc       240
ctatcccgac ttccttctcc ccaccgtcac ctccgccgcc gcgccgccgc cacagtacga       300
tcgcgtgcct ccgcacgcct tcgtccactt tgcgcgcccg gagggcgcgc gcgccgccgc       360
cgacgcaagc gggccgatcc gagctcatcc tytccggcaa acccctgcgc gccgcctccg       420
cacaggacag ctcccttcgg gcatcccgcc gccgtaagtg tctcgccatt ccgcttccct       480
ggctcgcgcc tcgaggtcgg ggnntctccc ggcctcggac gccttcatcg ccgcctggcg       540
cggccccggc ctctgggctc gagttctccg tcgacccgtt cgacgggtct tgccncttca       600
tcttcgcccg cgacaccgct ttcaaagtcc gggagttccg cgagtctgtg gtgatgcgct       660
gcgacgtcaa gctccagttc cccgtccgcg atgttgcgga agtcagggtg ttccggctcg       720
actgctcgct gctgatccgg ctatcggccg caccgctggt ctgttaccgc acggcggatg       780
acgacatcca cgtgtccgtg ccgttcgacc tgctcgacga cgatgacccg tggatacgga       840
ccacggacat cactccaagt ggtgcgattg ggcggtgcgg tgcgtataga atcacattct       900
cgccgcggtt ctggccaaag atggaacgcg cgctgacgta catgagggat aggagggtgg       960
cgatccttga ttgcgttgsa gggtgggggg ccaggagggg gctcaccgtg cgtgatgagc      1020
ctgagtttgg ggagcggatg caggacctgt tcttctgcgt gcagcacgcc gagggtctca      1080
agtttccggt gttgttcctc gtgaatgctc tggtgcacaa gggagtaata agtcaacacc      1140
```

```
acctcacgcc tgaattcttc ggtttgctcc agaggaagga ggatgatgtg aatgtggctg    1200
ccttgaggga attttggggg gacaaatttc cagtttttga tgcatgtggg aggctgaaga    1260
atctgcagga tagggttgcc aggtacctga aacatcttcg caacaagatt ggggatgtca    1320
attctgaggt gaggaggctg gtaatcacgc ccaccaaggc ttattgcatg ccaccagaag    1380
tggagcgctc taatcgcgtc atccggcatt atagtgaagt ctcagaccgg tttctgaggg    1440
ttacttttat ggatgaggga atgcagatgc tcaacagtaa tgtgctgaat ttctctgctg    1500
cacaaatcgt caaagatttg atgtcaaact cgttcctgca taagacaaca gtgtacaagc    1560
gtgttaaaac gttttttgaca gagggattcc acatgtgtgg caggaagtac tcgtttcttg    1620
cattctcatc taaccagctg agggacaggt cagcatggtt cttcgcagag gacagaacga    1680
caacagtgga aaccattagg aaatggatgg ggcggttcac aagtaagaat gtagcaaagc    1740
atgccgctcg gatggggcag tgcttctcct ctacatatgc tacggtggtg ctgcagccgc    1800
atgaggtaaa tgagtgtctt gatgaagttg aacataacgg gtacattttc tctgatggaa    1860
ttggcaagat tacgtgcgac cttgcactcg aagttgctca aagctgcaa ttgacagata    1920 atcccccatc tgcttaccag attaggtatg caggcttcaa gggtgttata tctgtctggg    1980
aaggaaaaaa tgatgggata cgactttccc tgaggccgag catgcacaag tttgagtcta    2040
accatactgt gttagaggtg gtctcgtgga caaagtttca gccaggattc ttaaatcgtc    2100
agattattac attactgtcc tccttgaatg tcccggatgc tatctttgct caaatgcagg    2160
aagccatgtt atctaatctc aacaatattt tgtcagactc tgatgttgct tttgacattg    2220
taaccgcctc ttgtgctgag caaggaacca ctgcagcact gatgttgagt gctggcattt    2280
cacctggaac tgagccacac ctgaaagcaa tgctgttagc tataaggtcc tcacagctgc    2340
taggtctttt ggagaagaca aggatttttg tgcccaaggg aaggtggttg atgggctgcc    2400
ttgatgaact tgggatcctt gagcaagggc agtgctttat ccgggcatca tctccatcac    2460
tcaataattg tctggtgaag tatggatcaa gattgtctgc agcaaacaca aatgcagaga    2520
ccattctggg tactatcgta atggcaaaga atccatgcct tcatccaggg gatgtccgaa    2580
tccttgaagc tgttgatgtg cctgaactgc atcaccttgt tgattgcttg gtcttcccca    2640
agaaaggtga gaggccgcac gcgaatgaag catctgggag tgatcttgat ggggatctat    2700
acttcgtaac atgggatgaa aaccttatac cacctggtaa aaagagttgg aaccctatgg    2760
actactcccc agctgaagca aaacaactgc cacgcgcagt atcccaacat gatattgttg    2820
gtttcttctt gaagaacatg gtaaatgaga aactgggtcc aataagcaat gctcatgttg    2880
ttcacgctga tatgagcgag tatgagcaa tggatgagaa gtgtattcag ttggcagaac    2940
tagcagcaac tgctgtggac ttccccaaga caggcaaaat tgtgtcaatg ccagcatccc    3000
ttcgaccaaa attatatcct gacttcatgg gaaaggagga tgctatctcc tatagatcag    3060
agaagatcct tggaaggctt tatcggtcaa tccaagaagc ctccagcgat gatttggttc    3120
cagaagaaac ttgcacatct aacaatctgc cttatgatgc agatatggaa gttgctggtg    3180
cagctgattt tctctcgagt gcttggcagt gcaagtgctc atatgaaaca caactgaacg    3240
cactgctcaa ccaatatggc gtgcgcactg aagcagagct tgtgacagag catatatggt    3300
cgcttcccaa gtacagcagc agaaggcagg gggacataaa ggagaggttg aagaatgcat    3360
actatgctct tcacaaggag tttaggagca ttttcgaaag cattgtgaca gatcaaacag    3420
agatctctga tgatgagaaa agtcggtttt acgagatgaa ggcctccgct tggtaccagg    3480
taacctacca tcctgaatgg gtccagaagt caagggaaat gttcaagtct gactgtgagg    3540
```

-continued

```
acatgccagc aaggcttagc tttgcatgga tcgcggttga gcacctggca cggattaaga    3600
taaggtgccg tggagaagtg aaagtggaca gcccaaggcc tgttgagagg ctcgcagcct    3660
acatatctgg gagcatgtga gttgacgtga agctccaagc aattgtgaag caagaccact    3720
ctgccctctt tgccatgcca tctgaactct gatgcatggc tctgtctagt cacttctttt    3780
tacgaattat tacatagttg agacacagcc actctataag cggctaaagc gtacgcacat    3840
ttctacgaac gataatgctt ttaagtctga actgttcaat ctctaaaaaa aaaaaaaaa    3900 g                                                                    3901
```

<210> SEQ ID NO 8
<211> LENGTH: 1164
<212> TYPE: PRT
<213> ORGANISM: Zea mays
<220> FEATURE:
<221> NAME/KEY: UNSURE
<222> LOCATION: (107)
<223> OTHER INFORMATION: Xaa = ANY AMINO ACID
<220> FEATURE:
<221> NAME/KEY: UNSURE
<222> LOCATION: (137)
<223> OTHER INFORMATION: Xaa = ANY AMINO ACID
<220> FEATURE:
<221> NAME/KEY: UNSURE
<222> LOCATION: (265)
<223> OTHER INFORMATION: Xaa = ANY AMINO ACID

<400> SEQUENCE: 8

```
Met Arg Ala Arg Ser Gly Ala Ala Leu Arg Pro Pro Gly Leu Arg
 1               5                  10                  15

Arg Thr Pro Ile Pro Thr Ser Phe Ser Pro Ser Pro Pro Pro
                20                  25                  30

Arg Arg Arg His Ser Thr Ile Ala Cys Leu Arg Thr Pro Ser Ser Thr
                35                  40                  45

Leu Arg Ala Arg Arg Ala Arg Pro Pro Thr Gln Ala Gly Arg
            50                  55                  60

Ser Glu Leu Ile Leu Ser Gly Lys Pro Leu Arg Ala Ala Ser Ala Gln
65                  70                  75                  80

Asp Ser Ser Leu Arg Ala Ser Arg Arg Lys Cys Leu Ala Ile Pro
                85                  90                  95

Leu Pro Trp Leu Ala Pro Arg Gly Arg Gly Xaa Ser Arg Pro Arg Thr
                100                 105                 110

Pro Ser Ser Pro Pro Gly Ala Ala Pro Ser Gly Leu Glu Phe Ser
            115                 120                 125

Val Asp Pro Phe Asp Gly Ser Cys Xaa Phe Ile Phe Ala Arg Asp Thr
130                 135                 140

Ala Phe Lys Val Arg Glu Phe Arg Glu Ser Val Val Met Arg Cys Asp
145                 150                 155                 160

Val Lys Leu Gln Phe Pro Val Arg Asp Val Ala Glu Val Arg Val Phe
                165                 170                 175

Arg Leu Asp Cys Ser Leu Leu Ile Arg Leu Ser Ala Ala Pro Leu Val
            180                 185                 190

Cys Tyr Arg Thr Ala Asp Asp Ile His Val Ser Val Pro Phe Asp
            195                 200                 205

Leu Leu Asp Asp Asp Pro Trp Ile Arg Thr Thr Asp Ile Thr Pro
    210                 215                 220

Ser Gly Ala Ile Gly Arg Cys Gly Ala Tyr Arg Ile Thr Phe Ser Pro
225                 230                 235                 240
```

-continued

```
Arg Phe Trp Pro Lys Met Glu Arg Ala Leu Thr Tyr Met Arg Asp Arg
                245                 250                 255
Arg Val Ala Ile Leu Asp Cys Val Xaa Gly Trp Gly Ala Arg Arg Gly
            260                 265                 270
Leu Thr Val Arg Asp Glu Pro Glu Phe Gly Arg Met Gln Asp Leu
        275                 280                 285
Phe Phe Cys Val Gln His Ala Glu Gly Leu Lys Phe Pro Val Leu Phe
    290                 295                 300
Leu Val Asn Ala Leu Val His Lys Gly Val Ile Ser Gln His His Leu
305                 310                 315                 320
Thr Pro Glu Phe Phe Gly Leu Leu Gln Arg Lys Glu Asp Asp Val Asn
                325                 330                 335
Val Ala Ala Leu Arg Glu Phe Trp Gly Asp Lys Phe Pro Val Phe Asp
            340                 345                 350
Ala Cys Gly Arg Leu Lys Asn Leu Gln Asp Arg Val Ala Arg Tyr Leu
        355                 360                 365
Lys His Leu Arg Asn Lys Ile Gly Asp Val Asn Ser Glu Val Arg Arg
    370                 375                 380
Leu Val Ile Thr Pro Thr Lys Ala Tyr Cys Met Pro Pro Glu Val Glu
385                 390                 395                 400
Arg Ser Asn Arg Val Ile Arg His Tyr Ser Glu Val Ser Asp Arg Phe
                405                 410                 415
Leu Arg Val Thr Phe Met Asp Glu Gly Met Gln Met Leu Asn Ser Asn
            420                 425                 430
Val Leu Asn Phe Ser Ala Ala Gln Ile Val Lys Asp Leu Met Ser Asn
        435                 440                 445
Ser Phe Leu His Lys Thr Thr Val Tyr Lys Arg Val Lys Thr Phe Leu
    450                 455                 460
Thr Glu Gly Phe His Met Cys Gly Arg Lys Tyr Ser Phe Leu Ala Phe
465                 470                 475                 480
Ser Ser Asn Gln Leu Arg Asp Arg Ser Ala Trp Phe Phe Ala Glu Asp
                485                 490                 495
Arg Thr Thr Thr Val Glu Thr Ile Arg Lys Trp Met Gly Arg Phe Thr
            500                 505                 510
Ser Lys Asn Val Ala Lys His Ala Ala Arg Met Gly Gln Cys Phe Ser
        515                 520                 525
Ser Thr Tyr Ala Thr Val Val Leu Gln Pro His Glu Val Asn Glu Cys
    530                 535                 540
Leu Asp Glu Val Glu His Asn Gly Tyr Ile Phe Ser Asp Gly Ile Gly
545                 550                 555                 560
Lys Ile Thr Cys Asp Leu Ala Leu Glu Val Ala Gln Lys Leu Gln Leu
                565                 570                 575
Thr Asp Asn Pro Pro Ser Ala Tyr Gln Ile Arg Tyr Ala Gly Phe Lys
            580                 585                 590
Gly Val Ile Ser Val Trp Glu Gly Lys Asn Asp Gly Ile Arg Leu Ser
        595                 600                 605
Leu Arg Pro Ser Met His Lys Phe Glu Ser Asn His Thr Val Leu Glu
    610                 615                 620
Val Val Ser Trp Thr Lys Phe Gln Pro Gly Phe Leu Asn Arg Gln Ile
625                 630                 635                 640
Ile Thr Leu Leu Ser Ser Leu Asn Val Pro Asp Ala Ile Phe Ala Gln
                645                 650                 655
```

-continued

```
Met Gln Glu Ala Met Leu Ser Asn Leu Asn Asn Ile Leu Ser Asp Ser
                660                 665                 670

Asp Val Ala Phe Asp Ile Val Thr Ala Ser Cys Ala Glu Gln Gly Thr
            675                 680                 685

Thr Ala Ala Leu Met Leu Ser Ala Gly Ile Ser Pro Gly Thr Glu Pro
        690                 695                 700

His Leu Lys Ala Met Leu Leu Ala Ile Arg Ser Ser Gln Leu Leu Gly
705                 710                 715                 720

Leu Leu Glu Lys Thr Arg Ile Phe Val Pro Lys Gly Arg Trp Leu Met
                725                 730                 735

Gly Cys Leu Asp Glu Leu Gly Ile Leu Glu Gln Gly Gln Cys Phe Ile
            740                 745                 750

Arg Ala Ser Ser Pro Ser Leu Asn Asn Cys Leu Val Lys Tyr Gly Ser
        755                 760                 765

Arg Leu Ser Ala Ala Asn Thr Asn Ala Glu Thr Ile Leu Gly Thr Ile
770                 775                 780

Val Met Ala Lys Asn Pro Cys Leu His Pro Gly Asp Val Arg Ile Leu
785                 790                 795                 800

Glu Ala Val Asp Val Pro Glu Leu His His Leu Val Asp Cys Leu Val
                805                 810                 815

Phe Pro Lys Lys Gly Glu Arg Pro His Ala Asn Glu Ala Ser Gly Ser
            820                 825                 830

Asp Leu Asp Gly Asp Leu Tyr Phe Val Thr Trp Asp Glu Asn Leu Ile
        835                 840                 845

Pro Pro Gly Lys Lys Ser Trp Asn Pro Met Asp Tyr Ser Pro Ala Glu
    850                 855                 860

Ala Lys Gln Leu Pro Arg Ala Val Ser Gln His Asp Ile Val Gly Phe
865                 870                 875                 880

Phe Leu Lys Asn Met Val Asn Glu Lys Leu Gly Pro Ile Ser Asn Ala
                885                 890                 895

His Val Val His Ala Asp Met Ser Glu Tyr Gly Ala Met Asp Glu Lys
            900                 905                 910

Cys Ile Gln Leu Ala Glu Leu Ala Ala Thr Ala Val Asp Phe Pro Lys
        915                 920                 925

Thr Gly Lys Ile Val Ser Met Pro Ala Ser Leu Arg Pro Lys Leu Tyr
    930                 935                 940

Pro Asp Phe Met Gly Lys Glu Asp Ala Ile Ser Tyr Arg Ser Glu Lys
945                 950                 955                 960

Ile Leu Gly Arg Leu Tyr Arg Ser Ile Gln Glu Ala Ser Ser Asp Asp
                965                 970                 975

Leu Val Pro Glu Glu Thr Cys Thr Ser Asn Asn Leu Pro Tyr Asp Ala
            980                 985                 990

Asp Met Glu Val Ala Gly Ala Ala Asp Phe Leu Ser Ser Ala Trp Gln
        995                 1000                1005

Cys Lys Cys Ser Tyr Glu Thr Gln Leu Asn Ala Leu Leu Asn Gln Tyr
    1010                1015                1020

Gly Val Arg Thr Glu Ala Gly Leu Val Thr Glu His Ile Trp Ser Leu
1025                1030                1035                1040

Pro Lys Tyr Ser Arg Arg Gln Gly Asp Ile Lys Glu Arg Leu Lys
                1045                1050                1055

Asn Ala Tyr Tyr Ala Leu His Lys Glu Phe Arg Ser Ile Phe Glu Ser
            1060                1065                1070

Ile Val Thr Asp Gln Thr Glu Ile Ser Asp Asp Glu Lys Ser Arg Phe
```

-continued

```
                          1075                 1080                 1085
 Tyr Glu Met Lys Ala Ser Ala Trp Tyr Gln Val Thr Tyr His Pro Glu
     1090                 1095                 1100

Trp Val Gln Lys Ser Arg Glu Met Phe Lys Ser Asp Cys Glu Asp Met
 1105                 1110                 1115                 1120

Pro Ala Arg Leu Ser Phe Ala Trp Ile Ala Val Glu His Leu Ala Arg
                 1125                 1130                 1135

Ile Lys Ile Arg Cys Arg Gly Glu Val Lys Val Asp Ser Pro Arg Pro
             1140                 1145                 1150

Val Glu Arg Leu Ala Ala Tyr Ile Ser Gly Ser Met
         1155                 1160

<210> SEQ ID NO 9
<211> LENGTH: 2816
<212> TYPE: DNA
<213> ORGANISM: Oryza sativa
<220> FEATURE:
<221> NAME/KEY: unsure
<222> LOCATION: (175)
<223> OTHER INFORMATION: n=a,c,g or t

<400> SEQUENCE: 9
gagaacgtca atgtggctgc attgagggat ttctgggggg acaagttccc agtgtttgat      60
gcgtgcggga ggctgaagaa ggcactgaat cgggtggcca ggaaccccaa acttctctgc     120
agcaaggtcg gggatgacca cgcggaggtg cggagcgtgg tgatcacgcc caccnaggct     180
tattgtctgc ctccagaagt ggagcgctca accgtgttc ttcggcatta ccatgaggtg      240
gctgacaggt ttttgagggt cacttttatg gacgagggta tgcaggtgct gaacaacaat     300
gtgctcaact ccttcactgc accaattgtc aaagacttga tgtcgaattt tttccagcag     360
aagacaacgg tgtacaagcg tgtcaggatg ttgttgacgg agggtttcca catgtgtgga     420
aggaagtact catttctcgc attctcatcg aaccagttaa gggacaagtc agcttggttc     480
tttgccgagg acagaaagac aacggtggaa gcaattagga agtggatgga cggttcacaa     540
gtaagaatgt tcgaagatgc tgctcgaatg gggcagtgct tctcatccac atatgcaact     600
gtgacaatgc ggccggatga ggttgatgag agttttgatg atgttgtgca taatgagtac     660
attttctccg atggaattgg caaaattacc ccagatcttg cattggaagt tgccgagagg     720
ctgcagctga cagataaccc gccatctgct tatcagatca ggtttgctgg cttcaagggt     780
gtcatagctg tctggcaagg acatggtgat gggacacggc ttttcctgag gccaagcatg     840
aggaagtttg agtctaacca tttggtgtta ggggtggtct cctggacaaa gttccagcca     900
ggattcttaa atcgacagat tataatattg ctatcctcac tgaatgtccc agattctatc     960
ttttggcaaa tgcaagagac catgctttct aacctcaaca atattctatc agacagagat    1020 gttgctttg aggttttaac aacttcatgt gctgatgatg aaacactgc agcattgatg      1080 ctcagtgctg gctttgaacc tagaactgaa ccacacttga aagcaatgct cttggctata    1140
aggtctgcac aattgcagga tcttttggaa aaagcaagga tatttgtgcc aaagggaagg    1200
tggttgatgg gctgtcttga tgagcttggg gttcttgagc aagggcagtg ctttattcgg    1260
gcaacagttc catcattgaa tagttatttt gttaagcatg ggtcaagatt tcatcaaca     1320 gataaaaaca cagaggtcat tttgggtact gtggtaatag caaagaatcc ctgtcttcat    1380 ccagggatg tccgcatcct tgaagcagtt gatgtgcccg aactgcatca tctggttgat     1440
tgtttggtgt tcccccagaa aggtgagagg ccacatgcta acgaggcatc tgggagcgat    1500
```

-continued

```
cttgatgggg atctctactt tgtgacatgg gatgagaaac ttatacctcc aggcaagaag    1560
agctggaacc ctatggacta ctcccccacct gaagcaaaac aacttccgcg ccaagtatct   1620
caacatgata tcattgattt cttcttaaag aacatgataa gtgagaatct tggtaggatc   1680
tgtaatgctc atgttgttca tgctgatctt agcgagtatg gtgcaatgga tgagaagtgt   1740
attcacttag ctgagctagc agcaactgcc gtggacttcc ccaagactgg caaacttgcg   1800
ataatgccac cacaccttaa accaaaagtc taccctgact tcatgggaaa ggaagatgga   1860 caatctttata aatcagaaaa gattcttgga aggctttatc gttcaatcca agaggcctcc   1920
aatggtgatg tggtgtcaca agaggtttgc actccaaatg atctgcctta tgacatagat   1980
ctggaagttc ctggtgcatc agatttcctc gcgagtgctt ggcaatgcaa gtgttcatac   2040
gacgcgcagc tgagtgcgct gctcagtcag tacagggtcc gcactgaagc tgaacttgtg   2100
acagggcaca taacgttcct tgttaagaac agcagcaaga agcaaggcga cataaaggac   2160
aggctgaaga ctgcttactc tgcactacgc aaggagttca aaagtacctt tgagagcata   2220
gcatcggatc aatgcgagat tggtgatgac gagaagaatc tgctgtacga gatgaaggcc   2280
tctgcctggt accaggtgac ctatcacccc aaatgggtgg agaagtcgag gggcattctg   2340
ggcccagatg gtgaggaaat accggcaagc cttagctttg catggatccc ggtggattac   2400
ttggcgcgga taaagctaag gtgccatggt aaagtgagag ttgaaggcca aaagcctgtt   2460
gaaaggcttg cagcatacat ctccgagagg atatgatgaa acaatgcaaa ggtcgcagta   2520
agaccactct gccattcgta atgccggttc aaagggcatg cgtacaaaat atctgagttt   2580
tttttctttt tcatttttgt tcacttcact gaacttgatc tcccgaatgt ttcagtgtgc   2640
ttttgttcct tcttacatgc ccctcaagcc tgaaaaactg tacgtttcag ttgagggctg   2700
tctatattat gaaatgcaca aatatacgct gcctgcagct tttggcaata tttcaagttc   2760
aggttgtgcg tcaaaaaaaa aaaaaaaaaa aaaaaaaaaa aaaaaaaaaa aaaaaa       2816
```

<210> SEQ ID NO 10
<211> LENGTH: 836
<212> TYPE: PRT
<213> ORGANISM: Oryza sativa
<220> FEATURE:
<221> NAME/KEY: UNSURE
<222> LOCATION: (2)
<223> OTHER INFORMATION: Xaa = ANY AMINO ACID
<220> FEATURE:
<221> NAME/KEY: UNSURE
<222> LOCATION: (64)
<223> OTHER INFORMATION: Xaa = ANY AMINO ACID

<400> SEQUENCE: 10

```
Met Xaa Arg Ser Glu Glu Asn Val Asn Val Ala Ala Leu Arg Asp Phe
 1               5                  10                  15

Trp Gly Asp Lys Phe Pro Val Phe Asp Ala Cys Gly Arg Leu Lys Lys
                20                  25                  30

Ala Leu Asn Arg Val Ala Arg Asn Pro Lys Leu Leu Cys Ser Lys Val
            35                  40                  45

Gly Asp Asp His Ala Glu Val Arg Ser Val Val Ile Thr Pro Thr Xaa
        50                  55                  60

Ala Tyr Cys Leu Pro Pro Glu Val Glu Arg Ser Asn Arg Val Leu Arg
    65                  70                  75                  80

His Tyr His Glu Val Ala Asp Arg Phe Leu Arg Val Thr Phe Met Asp
                85                  90                  95

Glu Gly Met Gln Val Leu Asn Asn Asn Val Leu Asn Ser Phe Thr Ala
```

-continued

```
            100                 105                 110
Pro Ile Val Lys Asp Leu Met Ser Asn Phe Phe Gln Gln Lys Thr Thr
            115                 120                 125
Val Tyr Lys Arg Val Arg Met Leu Leu Thr Glu Gly Phe His Met Cys
            130                 135             140
Gly Arg Lys Tyr Ser Phe Leu Ala Phe Ser Ser Asn Gln Leu Arg Asp
145                 150                 155                 160
Lys Ser Ala Trp Phe Phe Ala Glu Asp Arg Lys Thr Thr Val Glu Ala
                    165                 170             175
Ile Arg Lys Trp Met Asp Gly Ser Gln Val Arg Met Phe Glu Asp Ala
                180                 185                 190
Ala Arg Met Gly Gln Cys Phe Ser Ser Thr Tyr Ala Thr Val Thr Met
            195                 200                 205
Arg Pro Asp Glu Val Asp Glu Ser Phe Asp Asp Val His Asn Glu
            210                 215                 220
Tyr Ile Phe Ser Asp Gly Ile Gly Lys Ile Thr Pro Asp Leu Ala Leu
225                 230                 235                 240
Glu Val Ala Glu Arg Leu Gln Leu Thr Asp Asn Pro Pro Ser Ala Tyr
                    245                 250                 255
Gln Ile Arg Phe Ala Gly Phe Lys Gly Val Ile Ala Val Trp Gln Gly
                260                 265                 270
His Gly Asp Gly Thr Arg Leu Phe Leu Arg Pro Ser Met Arg Lys Phe
            275                 280                 285
Glu Ser Asn His Leu Val Leu Gly Val Val Ser Trp Thr Lys Phe Gln
            290                 295                 300
Pro Gly Phe Leu Asn Arg Gln Ile Ile Ile Leu Leu Ser Ser Leu Asn
305                 310                 315                 320
Val Pro Asp Ser Ile Phe Trp Gln Met Gln Glu Thr Met Leu Ser Asn
                    325                 330                 335
Leu Asn Asn Ile Leu Ser Asp Arg Asp Val Ala Phe Glu Val Leu Thr
                340                 345                 350
Thr Ser Cys Ala Asp Asp Gly Asn Thr Ala Ala Leu Met Leu Ser Ala
            355                 360                 365
Gly Phe Glu Pro Arg Thr Glu Pro His Leu Lys Ala Met Leu Leu Ala
        370                 375                 380
Ile Arg Ser Ala Gln Leu Gln Asp Leu Leu Glu Lys Ala Arg Ile Phe
385                 390                 395                 400
Val Pro Lys Gly Arg Trp Leu Met Gly Cys Leu Asp Glu Leu Gly Val
                    405                 410                 415
Leu Glu Gln Gly Gln Cys Phe Ile Arg Ala Thr Val Pro Ser Leu Asn
                420                 425                 430
Ser Tyr Phe Val Lys His Gly Ser Arg Phe Ser Ser Thr Asp Lys Asn
            435                 440                 445
Thr Glu Val Ile Leu Gly Thr Val Val Ile Ala Lys Asn Pro Cys Leu
            450                 455                 460
His Pro Gly Asp Val Arg Ile Leu Glu Ala Val Asp Val Pro Glu Leu
465                 470                 475                 480
His His Leu Val Asp Cys Leu Val Phe Pro Gln Lys Gly Glu Arg Pro
                    485                 490                 495
His Ala Asn Glu Ala Ser Gly Ser Asp Leu Asp Gly Asp Leu Tyr Phe
                500                 505                 510
Val Thr Trp Asp Glu Lys Leu Ile Pro Pro Gly Lys Lys Ser Trp Asn
            515                 520                 525
```

Pro Met Asp Tyr Ser Pro Pro Glu Ala Lys Gln Leu Pro Arg Gln Val
    530                 535                 540

Ser Gln His Asp Ile Ile Asp Phe Phe Leu Lys Asn Met Ile Ser Glu
545                 550                 555                 560

Asn Leu Gly Arg Ile Cys Asn Ala His Val His Ala Asp Leu Ser
                565                 570                 575

Glu Tyr Gly Ala Met Asp Glu Lys Cys Ile His Leu Ala Glu Leu Ala
                580                 585                 590

Ala Thr Ala Val Asp Phe Pro Lys Thr Gly Lys Leu Ala Ile Met Pro
        595                 600                 605

Pro His Leu Lys Pro Lys Val Tyr Pro Asp Phe Met Gly Lys Glu Asp
        610                 615                 620

Gly Gln Ser Tyr Lys Ser Glu Lys Ile Leu Gly Arg Leu Tyr Arg Ser
625                 630                 635                 640

Ile Gln Glu Ala Ser Asn Gly Asp Val Val Ser Gln Glu Val Cys Thr
                645                 650                 655

Pro Asn Asp Leu Pro Tyr Asp Ile Asp Leu Glu Val Pro Gly Ala Ser
                660                 665                 670

Asp Phe Leu Ala Ser Ala Trp Gln Cys Lys Cys Ser Tyr Asp Ala Gln
        675                 680                 685

Leu Ser Ala Leu Leu Ser Gln Tyr Arg Val Arg Thr Glu Ala Glu Leu
        690                 695                 700

Val Thr Gly His Ile Thr Phe Leu Val Lys Asn Ser Ser Lys Lys Gln
705                 710                 715                 720

Gly Asp Ile Lys Asp Arg Leu Lys Thr Ala Tyr Ser Ala Leu Arg Lys
                725                 730                 735

Glu Phe Lys Ser Thr Phe Glu Ser Ile Ala Ser Asp Gln Cys Glu Ile
                740                 745                 750

Gly Asp Asp Glu Lys Asn Leu Leu Tyr Glu Met Lys Ala Ser Ala Trp
        755                 760                 765

Tyr Gln Val Thr Tyr His Pro Lys Trp Val Glu Lys Ser Arg Gly Ile
        770                 775                 780

Leu Gly Pro Asp Gly Glu Ile Pro Ala Ser Leu Ser Phe Ala Trp
785                 790                 795                 800

Ile Pro Val Asp Tyr Leu Ala Arg Ile Lys Leu Arg Cys His Gly Lys
                805                 810                 815

Val Arg Val Glu Gly Gln Lys Pro Val Glu Arg Leu Ala Ala Tyr Ile
        820                 825                 830

Ser Glu Arg Ile
        835

<210> SEQ ID NO 11
<211> LENGTH: 3807
<212> TYPE: DNA
<213> ORGANISM: Glycine max

<400> SEQUENCE: 11
gcacgaggag ggttagtgag tgttgttgac ttcacattga cgatcctttt tttttcctgt    60
ctgtttgctt ccaatttctc ataccttcaa tcttcaatct tggaagattg gagaacagca   120
ttgattgagt tttaccacac gatcgtagag cttctgatat ttttcgaaga ggaaaggcaa   180
aagagttagc atttaggatg ggaaaaacaa ttgagttgta tggattccct acatctgtga   240
atgtgtctga tgtaaagaca tttgtagagc agtatactgg tgaaggaact gtgttcgcca   300

| | |
|---|---|
| ttaaattaag acatggaaaa ggtcgggttc aagagcatt tgcaattatt caattcacca | 360 |
| ccgcaaattc tgctacatct atgatgtcca gagctaacaa cattttgaga acattgcggt | 420 |
| atgggacctc ctatttaaaa gctcgggaaa tggaaagaga tattgtgcca aggccaaggg | 480 |
| tgttttttgca tagtttggat gatgtgaaac tgtcttttgg ctgtcagatc tcaaagggaa | 540 |
| gattctctgt tttatggaaa aagcaggatg ttattgtaaa ttttgggagt ggaatgagaa | 600 |
| agatgcattt cttattttcc cacaacaatg tgcaatacaa acttgagctt tcatatgaga | 660 |
| acatttggaa gattgagctg catcggccac ggaatgagac tacacgttat ctgttgattc | 720 |
| agttacttgg tgctccccgg ttttttgaga acgatgtacc tacatcaaca aatatctttg | 780 |
| atgatccttt gttcaacttc ttcaaagatg cccctgatga gcaatggatc cgagcaattg | 840 |
| atttcactcc agaaagtcgt attgggcagt cctccgccat atgtctggag cttcctaatg | 900 |
| gccgacaact tccaaatttc agggaaaact ttgcttatta tgaggaaagt gagaggcaat | 960 |
| acactttaca gacaggagtt ccctttttctc aaaattgggg tcttgtcccc attgttgctc | 1020 |
| ctcctctagg tgttaaaata tcatatgaca tcttgtttaa agtcaattca ttggttcaac | 1080 |
| atgcatgtct tgcaggacct gcacttgatg gtgacttcta tcgcttggtt gatccacgta | 1140 |
| gaatgccccg tgaatttatt gaatatgctt tagaaaagat ttactattca aaggaatttt | 1200 |
| gttatgaacc cacaaagtgg ctgactgatc agtacaaaac ataccttgag tcaaaaaatc | 1260 |
| atcctcggtc acctgcaata tccttggata cagggttggt atacgttcgc agggttcaga | 1320 |
| tcacgccttg caaagtatac ttttgtggtc cagagatgaa tgtctcaaat cgtgttctcc | 1380 |
| gtcatttccg tgaacatatt gataactttc tacgtgtttc atttgttgat gaagaattgg | 1440 |
| ataaactgtt ttcaactgat ttatcatcac gttcacagaa caagaaaact gagatataca | 1500 |
| ccagaattct ttccatcctt aagaatggca tagttgttgg tgataagaag tttgaatttc | 1560 |
| tagcattctc atcaagtcag ttgcgggaaa actctctctg gatgtttgct cctacagaaa | 1620 |
| ctggatgtac tgctgcttac ataaggaaat ggatgggaaa ttttagccag attaggaatg | 1680 |
| ttgctaaaata tgctgctagg ctggggcaat cttttggttc atctactgaa actctaagtg | 1740 |
| tccataggga tgaagttgaa attattcctg atgtgaagaa gcttacatat gatggaaacg | 1800 |
| aatatgtctt ctctgatgga attgggaaaa tatctcttga atttgcccag aaagtggcta | 1860 |
| aaaaatgtgg ttatgattgc actccatctg cctttcagat tcgatatggt gggtacaaag | 1920 |
| gagttgtggc tgttgacccct aaatcatgct acaagttatc actgaggaag agcatgcgga | 1980 |
| agtatgattc agataacaca aagttagatg ttttggcccg tagtaagttt cagccatgtt | 2040 |
| atctgaatcg gcagttaatt tctctcttat ccactcttgg tatcaaggat gatgtttttg | 2100 |
| agaaaaaaca aagagaaact gttaatcaac tgaacactat actaacagat tcattaaagg | 2160 |
| ctcaggaagt tctggactta atgtctgctg gagagatcac taatgttctg aaggagatgc | 2220 |
| tcatttgtgg atacaagcct aatgaagaac cattcctttc aatgatgctt caaacattta | 2280 |
| gggcatcaaa acttttggaa ttgcgactta aatctaggat ctttattcca aaaggaagag | 2340 |
| caatgatggg atgtctagat gaaactagaa ccctagaata tggtcaagta tttgttcagt | 2400 |
| tctctaacaa taggctgcag aatctatctg atgattttt ttcatatgat ttgccaaaga | 2460 |
| attatatggt taaaggtaag gtagttgtag caaaaaaycc ctgcttgcac ccaggtgatg | 2520 |
| tgcgtgtttt acaagctgtg gatgtgccag atttgtacca catggtggac tgtgttgttt | 2580 |
| tccctcaaaa aggaccaaga cctcatccaa atgagtgttc gggaagtgat ctggatggag | 2640 |
| atatctactt tgtttgttgg gaccatgaat tgattccttc tcgcccaatt gatccaatgg | 2700 |

```
actatactgc tccygcaact gtggaattgg atcatgatgt gatgatcgag gaggttgagg    2760
agtattttgc caattacata gtcaatgaca gtctgggaat aattgccaat gcacacactg    2820
tctttgcaga taaagaacat ttgaaagcaa tgtctgatca atgtgttaag cttgcaaggt    2880
tgttttcaac agcagttgac tttcctaaaa ctggtgttcc agctgttata cctcctgaac    2940
ttcatgtcaa agaatatcct gacttcatgg agaagcctga caaacccaca tacaaatcgc    3000
ataacgtgat aggaaagctc tttagggaag tgaaagaaat atcaacaagt gccggctcaa    3060
ttacatcctt cacaaagttg gttgcgagag actcttacga ccatgaaatg gaagttgatg    3120
gcttcatgga ttatgttgat gatgctttct atcacaaaac caattatgac tacaagttgg    3180
gaaatctgat ggactactat gggatcaaaa ctgaagctga atcctcggt gggaatatta    3240 tgaaaatgtc aaaatctttc aacaaaagga gggatgcaga agcaatcaat atggctgtga    3300
ggtccctaag gaaagaggcc agggcctggt tcaatgaaaa cagcagtggt gatgtagatt    3360
cagggagtag tgatgtgtat gcaaaagctt ctgcttggta ccatgttact tatcatccaa    3420
gttactgggg ttgctataat gaaggcatga atagggatca ttatctaagt ttctcatggt    3480
gtgtttaccc tcttcttgtc caaatcaaga aagagaaact cagcattaga aggtcctctt    3540
tggaatacag tttcagtggg ttgcgtttga gttgacaact ttggactttg cactccctat    3600
tttccagttg gatttctgag ccaggcagct tgtttatatt tttatagtaa ctatgcatgt    3660
atgttctatg gtaatgtcgc tatataacat gtatgagtga atatatacat attctatcaa    3720
ggaatgaggg tgtgcacttc cattcccttg ctttttttaa aattatatat aaatattttg    3780
aatgtgtaaa aaaaaaaaaa aaaaagc                                        3807
```

<210> SEQ ID NO 12
<211> LENGTH: 1125
<212> TYPE: PRT
<213> ORGANISM: Glycine max

<400> SEQUENCE: 12

```
Met Gly Lys Thr Ile Glu Leu Tyr Gly Phe Pro Thr Ser Val Asn Val
 1               5                  10                  15

Ser Asp Val Lys Thr Phe Val Glu Gln Tyr Thr Gly Glu Gly Thr Val
            20                  25                  30

Phe Ala Ile Lys Leu Arg His Gly Lys Gly Arg Val Pro Arg Ala Phe
        35                  40                  45

Ala Ile Ile Gln Phe Thr Thr Ala Asn Ser Ala Thr Ser Met Met Ser
    50                  55                  60

Arg Ala Asn Asn Ile Leu Arg Thr Leu Arg Tyr Gly Thr Ser Tyr Leu
65                  70                  75                  80

Lys Ala Arg Glu Met Glu Arg Asp Ile Val Pro Arg Pro Arg Val Phe
                85                  90                  95

Leu His Ser Leu Asp Asp Val Lys Leu Ser Phe Gly Cys Gln Ile Ser
            100                 105                 110

Lys Gly Arg Phe Ser Val Leu Trp Lys Lys Gln Asp Val Ile Val Asn
        115                 120                 125

Phe Gly Ser Gly Met Arg Lys Met His Phe Leu Phe Ser His Asn Asn
    130                 135                 140

Val Gln Tyr Lys Leu Glu Leu Ser Tyr Glu Asn Ile Trp Lys Ile Glu
145                 150                 155                 160

Leu His Arg Pro Arg Asn Glu Thr Thr Arg Tyr Leu Leu Ile Gln Leu
                165                 170                 175
```

-continued

Leu Gly Ala Pro Arg Val Phe Glu Asn Asp Val Pro Thr Ser Thr Asn
            180                 185                 190

Ile Phe Asp Asp Pro Leu Phe Asn Phe Phe Lys Asp Ala Pro Asp Glu
            195                 200                 205

Gln Trp Ile Arg Ala Ile Asp Phe Thr Pro Glu Ser Arg Ile Gly Gln
            210                 215                 220

Ser Ser Ala Ile Cys Leu Glu Leu Pro Asn Gly Arg Gln Leu Pro Asn
225                 230                 235                 240

Phe Arg Glu Asn Phe Ala Tyr Tyr Glu Glu Ser Glu Arg Gln Tyr Thr
                245                 250                 255

Leu Gln Thr Gly Val Pro Phe Ser Gln Asn Trp Gly Leu Val Pro Ile
            260                 265                 270

Val Ala Pro Pro Leu Gly Val Lys Ile Ser Tyr Asp Ile Leu Phe Lys
            275                 280                 285

Val Asn Ser Leu Val Gln His Ala Cys Leu Ala Gly Pro Ala Leu Asp
            290                 295                 300

Gly Asp Phe Tyr Arg Leu Val Asp Pro Arg Arg Met Pro Arg Glu Phe
305                 310                 315                 320

Ile Glu Tyr Ala Leu Glu Lys Ile Tyr Tyr Ser Lys Glu Phe Cys Tyr
                325                 330                 335

Glu Pro Thr Lys Trp Leu Thr Asp Gln Tyr Lys Thr Tyr Leu Glu Ser
            340                 345                 350

Lys Asn His Pro Arg Ser Pro Ala Ile Ser Leu Asp Thr Gly Leu Val
            355                 360                 365

Tyr Val Arg Arg Val Gln Ile Thr Pro Cys Lys Val Tyr Phe Cys Gly
            370                 375                 380

Pro Glu Met Asn Val Ser Asn Arg Val Leu Arg His Phe Arg Glu His
385                 390                 395                 400

Ile Asp Asn Phe Leu Arg Val Ser Phe Val Asp Glu Glu Leu Asp Lys
                405                 410                 415

Leu Phe Ser Thr Asp Leu Ser Ser Arg Ser Gln Asn Lys Lys Thr Glu
            420                 425                 430

Ile Tyr Thr Arg Ile Leu Ser Ile Leu Lys Asn Gly Ile Val Val Gly
            435                 440                 445

Asp Lys Lys Phe Glu Phe Leu Ala Phe Ser Ser Gln Leu Arg Glu
            450                 455                 460

Asn Ser Leu Trp Met Phe Ala Pro Thr Glu Thr Gly Cys Thr Ala Ala
465                 470                 475                 480

Tyr Ile Arg Lys Trp Met Gly Asn Phe Ser Gln Ile Arg Asn Val Ala
                485                 490                 495

Lys Tyr Ala Ala Arg Leu Gly Gln Ser Phe Gly Ser Ser Thr Glu Thr
            500                 505                 510

Leu Ser Val His Arg Asp Glu Val Glu Ile Ile Pro Asp Val Lys Lys
            515                 520                 525

Leu Thr Tyr Asp Gly Asn Glu Tyr Val Phe Ser Asp Gly Ile Gly Lys
            530                 535                 540

Ile Ser Leu Glu Phe Ala Gln Lys Val Ala Lys Lys Cys Gly Tyr Asp
545                 550                 555                 560

Cys Thr Pro Ser Ala Phe Gln Ile Arg Tyr Gly Gly Tyr Lys Gly Val
                565                 570                 575

Val Ala Val Asp Pro Lys Ser Cys Tyr Lys Leu Ser Leu Arg Lys Ser
            580                 585                 590

```
Met Arg Lys Tyr Asp Ser Asp Asn Thr Lys Leu Asp Val Leu Ala Arg
        595                 600                 605

Ser Lys Phe Gln Pro Cys Tyr Leu Asn Arg Gln Leu Ile Ser Leu Leu
        610                 615                 620

Ser Thr Leu Gly Ile Lys Asp Val Phe Glu Lys Lys Gln Arg Glu
625                 630                 635                 640

Thr Val Asn Gln Leu Asn Thr Ile Leu Thr Asp Ser Leu Lys Ala Gln
                    645                 650                 655

Glu Val Leu Asp Leu Met Ser Ala Gly Glu Ile Thr Asn Val Leu Lys
            660                 665                 670

Glu Met Leu Ile Cys Gly Tyr Lys Pro Asn Glu Pro Phe Leu Ser
        675                 680                 685

Met Met Leu Gln Thr Phe Arg Ala Ser Lys Leu Leu Glu Leu Arg Leu
        690                 695                 700

Lys Ser Arg Ile Phe Ile Pro Lys Gly Arg Ala Met Met Gly Cys Leu
705                 710                 715                 720

Asp Glu Thr Arg Thr Leu Glu Tyr Gly Gln Val Phe Val Gln Phe Ser
                    725                 730                 735

Asn Asn Arg Leu Gln Asn Leu Ser Asp Asp Phe Phe Ser Tyr Asp Leu
            740                 745                 750

Pro Lys Asn Tyr Met Val Lys Gly Lys Val Val Ala Lys Asn Pro
        755                 760                 765

Cys Leu His Pro Gly Asp Val Arg Val Leu Gln Ala Val Asp Val Pro
        770                 775                 780

Asp Leu Tyr His Met Val Asp Cys Val Val Phe Pro Gln Lys Gly Pro
785                 790                 795                 800

Arg Pro His Pro Asn Glu Cys Ser Gly Ser Asp Leu Asp Gly Asp Ile
                    805                 810                 815

Tyr Phe Val Cys Trp Asp His Glu Leu Ile Pro Ser Arg Pro Ile Asp
            820                 825                 830

Pro Met Asp Tyr Thr Ala Pro Ala Thr Val Glu Leu Asp His Asp Val
        835                 840                 845

Met Ile Glu Glu Val Glu Tyr Phe Ala Asn Tyr Ile Val Asn Asp
        850                 855                 860

Ser Leu Gly Ile Ile Ala Asn Ala His Thr Val Phe Ala Asp Lys Glu
865                 870                 875                 880

His Leu Lys Ala Met Ser Asp Gln Cys Val Lys Leu Ala Arg Leu Phe
                    885                 890                 895

Ser Thr Ala Val Asp Phe Pro Lys Thr Gly Val Pro Ala Val Ile Pro
            900                 905                 910

Pro Glu Leu His Val Lys Glu Tyr Pro Asp Phe Met Glu Lys Pro Asp
        915                 920                 925

Lys Pro Thr Tyr Lys Ser His Asn Val Ile Gly Lys Leu Phe Arg Glu
        930                 935                 940

Val Lys Glu Ile Ser Thr Ser Ala Gly Ser Ile Thr Ser Phe Thr Lys
945                 950                 955                 960

Leu Val Ala Arg Asp Ser Tyr Asp His Glu Met Glu Val Asp Gly Phe
                    965                 970                 975

Met Asp Tyr Val Asp Asp Ala Phe Tyr His Lys Thr Asn Tyr Asp Tyr
            980                 985                 990

Lys Leu Gly Asn Leu Met Asp Tyr Tyr Gly Ile Lys Thr Glu Ala Glu
        995                 1000                1005

Ile Leu Gly Gly Asn Ile Met Lys Met Ser Lys Ser Phe Asn Lys Arg
```

```
                1010                1015                1020
Arg Asp Ala Glu Ala Ile Asn Met Ala Val Arg Ser Leu Arg Lys Glu
1025                1030                1035                1040

Ala Arg Ala Trp Phe Asn Glu Asn Ser Ser Gly Asp Val Asp Ser Gly
                1045                1050                1055

Ser Ser Asp Val Tyr Ala Lys Ala Ser Ala Trp Tyr His Val Thr Tyr
                1060                1065                1070

His Pro Ser Tyr Trp Gly Cys Tyr Asn Glu Gly Met Asn Arg Asp His
           1075                1080                1085

Tyr Leu Ser Phe Ser Trp Cys Val Tyr Pro Leu Leu Val Gln Ile Lys
     1090                1095                1100

Lys Glu Lys Leu Ser Ile Arg Arg Ser Ser Leu Glu Tyr Ser Phe Ser
1105                1110                1115                1120

Gly Leu Arg Leu Ser
           1125

<210> SEQ ID NO 13
<211> LENGTH: 740
<212> TYPE: DNA
<213> ORGANISM: Zea mays
<220> FEATURE:
<223> OTHER INFORMATION: n=a,c,g or t
<220> FEATURE:
<221> NAME/KEY: unsure
<222> LOCATION: (460)
<223> OTHER INFORMATION: n=a,c,g or t
<220> FEATURE:
<221> NAME/KEY: unsure
<222> LOCATION: (486)
<223> OTHER INFORMATION: n=a,c,g or t
<220> FEATURE:
<221> NAME/KEY: unsure
<222> LOCATION: (515)
<223> OTHER INFORMATION: n=a,c,g or t
<220> FEATURE:
<221> NAME/KEY: unsure
<222> LOCATION: (518)
<223> OTHER INFORMATION: n=a,c,g or t
<220> FEATURE:
<221> NAME/KEY: unsure
<222> LOCATION: (581)
<223> OTHER INFORMATION: n=a,c,g or t
<220> FEATURE:
<221> NAME/KEY: unsure
<222> LOCATION: (638)
<223> OTHER INFORMATION: n=a,c,g or t
<220> FEATURE:
<221> NAME/KEY: unsure
<222> LOCATION: (662)
<223> OTHER INFORMATION: n=a,c,g or t
<220> FEATURE:
<221> NAME/KEY: unsure
<222> LOCATION: (694)
<223> OTHER INFORMATION: n=a,c,g or t
<220> FEATURE:
<221> NAME/KEY: unsure
<222> LOCATION: (709)
<223> OTHER INFORMATION: n=a,c,g or t
<220> FEATURE:
<221> NAME/KEY: unsure
<222> LOCATION: (715)
<223> OTHER INFORMATION: n=a,c,g or t
<220> FEATURE:
<221> NAME/KEY: unsure
<222> LOCATION: (733)
<223> OTHER INFORMATION: n=a,c,g or t

<400> SEQUENCE: 13
cgccaatgcg catgtggtct ttgcagatca ggaacgtatg aaggctgaga gtccaccgtg    60
```

```
cgttcaactg gccaagctct tctctatagc tgtcgatttc ccaaagactg gagtgccggc      120
tctgattcca catgagctac atgtcaagga gtatcctgac ttcatggaga aactcgacaa      180
agtcacctat gaatcaaagg gtgtgatcgg gaagctctat agggaaataa agaagcacac      240
accacacata aagcacttca cgagggaagt ggcaaggcgg tcttatgaca ccgatttgat      300
tgttgatggc tatgaagatt acattactga ggctatagag ttcaaggaag agtacgattt      360
caggctgggt aatcttatgg accactatgg cataaaaagt gaagctgaga taataagtgg      420
atgtattcta aagatggcaa agaatttcac caagagtagn gatgctgatg caattagaat      480
ggcggngaga tctttgagga aagaagctag gtcgnggntc aatgagatga gcacaggaga      540
ggatggccaa gatgccatgg aggccaaggc ctctgcttgg naccatggta cttatcatca      600
gcagtactgg ggcagctaca atgaagggta tgatcggncg catcttatta gcttcccatg      660
gngcggatat gacaagcttg ggggcatcaa gcagggagg aatctcctna cgcanaatgg      720
atcgaaactt ganggtccgg                                                  740
```

<210> SEQ ID NO 14
<211> LENGTH: 230
<212> TYPE: PRT
<213> ORGANISM: Zea mays
<220> FEATURE:
<221> NAME/KEY: UNSURE
<222> LOCATION: (153)
<223> OTHER INFORMATION: Xaa = ANY AMINO ACID
<220> FEATURE:
<221> NAME/KEY: UNSURE
<222> LOCATION: (162)
<223> OTHER INFORMATION: Xaa = ANY AMINO ACID
<220> FEATURE:
<221> NAME/KEY: UNSURE
<222> LOCATION: (172)..(173)
<223> OTHER INFORMATION: Xaa = ANY AMINO ACID
<220> FEATURE:
<221> NAME/KEY: UNSURE
<222> LOCATION: (194)
<223> OTHER INFORMATION: Xaa = ANY AMINO ACID
<220> FEATURE:
<221> NAME/KEY: UNSURE
<222> LOCATION: (213)
<223> OTHER INFORMATION: Xaa = ANY AMINO ACID
<220> FEATURE:
<221> NAME/KEY: UNSURE
<222> LOCATION: (221)
<223> OTHER INFORMATION: Xaa = ANY AMINO ACID

<400> SEQUENCE: 14

```
Ala Asn Ala His Val Val Phe Ala Asp Gln Glu Arg Met Lys Ala Glu
 1               5                  10                  15

Ser Pro Pro Cys Val Gln Leu Ala Lys Leu Phe Ser Ile Ala Val Asp
            20                  25                  30

Phe Pro Lys Thr Gly Val Pro Ala Leu Ile Pro His Glu Leu His Val
        35                  40                  45

Lys Glu Tyr Pro Asp Phe Met Glu Lys Leu Asp Lys Val Thr Tyr Glu
    50                  55                  60

Ser Lys Gly Val Ile Gly Lys Leu Tyr Arg Glu Ile Lys Lys His Thr
65                  70                  75                  80

Pro His Ile Lys His Phe Thr Arg Glu Val Ala Arg Arg Ser Tyr Asp
                85                  90                  95

Thr Asp Leu Ile Val Asp Gly Tyr Glu Asp Tyr Ile Thr Glu Ala Ile
            100                 105                 110

Glu Phe Lys Glu Glu Tyr Asp Phe Arg Leu Gly Asn Leu Met Asp His
        115                 120                 125
```

```
Tyr Gly Ile Lys Ser Glu Ala Glu Ile Ile Ser Gly Cys Ile Leu Lys
        130                 135                 140

Met Ala Lys Asn Phe Thr Lys Ser Xaa Asp Ala Asp Ala Ile Arg Met
145                 150                 155                 160

Ala Xaa Arg Ser Leu Arg Lys Glu Ala Arg Ser Xaa Xaa Asn Glu Met
            165                 170                 175

Ser Thr Gly Glu Asp Gly Gln Asp Ala Met Glu Ala Lys Ala Ser Ala
        180                 185                 190

Trp Xaa His Gly Thr Tyr His Gln Gln Tyr Trp Gly Ser Tyr Asn Glu
            195                 200                 205

Gly Tyr Asp Arg Xaa His Leu Ile Ser Phe Pro Trp Xaa Gly Tyr Asp
        210                 215                 220

Lys Leu Gly Gly Ile Lys
225                 230

<210> SEQ ID NO 15
<211> LENGTH: 376
<212> TYPE: DNA
<213> ORGANISM: Oryza sativa
<220> FEATURE:
<221> NAME/KEY: unsure
<222> LOCATION: (17)
<223> OTHER INFORMATION: n=a,c,g or t
<220> FEATURE:
<221> NAME/KEY: unsure
<222> LOCATION: (31)
<223> OTHER INFORMATION: n=a,c,g or t
<220> FEATURE:
<221> NAME/KEY: unsure
<222> LOCATION: (48)
<223> OTHER INFORMATION: n=a,c,g or t
<220> FEATURE:
<221> NAME/KEY: unsure
<222> LOCATION: (160)
<223> OTHER INFORMATION: n=a,c,g or t
<220> FEATURE:
<221> NAME/KEY: unsure
<222> LOCATION: (187)
<223> OTHER INFORMATION: n=a,c,g or t
<220> FEATURE:
<221> NAME/KEY: unsure
<222> LOCATION: (216)
<223> OTHER INFORMATION: n=a,c,g or t
<220> FEATURE:
<221> NAME/KEY: unsure
<222> LOCATION: (219)
<223> OTHER INFORMATION: n=a,c,g or t
<220> FEATURE:
<221> NAME/KEY: unsure
<222> LOCATION: (230)
<223> OTHER INFORMATION: n=a,c,g or t
<220> FEATURE:
<221> NAME/KEY: unsure
<222> LOCATION: (281)
<223> OTHER INFORMATION: n=a,c,g or t
<220> FEATURE:
<221> NAME/KEY: unsure
<222> LOCATION: (309)
<223> OTHER INFORMATION: n=a,c,g or t
<220> FEATURE:
<221> NAME/KEY: unsure
<222> LOCATION: (334)
<223> OTHER INFORMATION: n=a,c,g or t
<220> FEATURE:
<221> NAME/KEY: unsure
<222> LOCATION: (340)
<223> OTHER INFORMATION: n=a,c,g or t
<220> FEATURE:
<221> NAME/KEY: unsure
<222> LOCATION: (345)..(346)
<223> OTHER INFORMATION: n=a,c,g or t
```

-continued

```
<220> FEATURE:
<221> NAME/KEY: unsure
<222> LOCATION: (355)
<223> OTHER INFORMATION: n=a,c,g or t
<220> FEATURE:
<221> NAME/KEY: unsure
<222> LOCATION: (357)
<223> OTHER INFORMATION: n=a,c,g or t
<220> FEATURE:
<221> NAME/KEY: unsure
<222> LOCATION: (361)
<223> OTHER INFORMATION: n=a,c,g or t

<400> SEQUENCE: 15
gttaaaggtg gtctccngga caaagttcca nccaggattc ttaaatcnac agattataat      60
attgctatcc tcactgaatg tcccagattc tatcttttgg caaatgcaag agaccatgct     120
ttctaacctc aacaatattc tatcagacag agatgttgcn tttgaggttt taacaacttc     180
atgtgcngat gatggaaaca ctgcagcatt gatgcncant gctggctttn aacctagaac     240
tgaaccacac ttgaaagcaa tgctcttggc gataaggtcc ngcacaattg caggatcttt     300
ttgaaaaanc aaggatattt gtgccaaacg gaangtgggn tgatnnggct gtccntnatt     360
naacctgggg gttctt                                                      376

<210> SEQ ID NO 16
<211> LENGTH: 111
<212> TYPE: PRT
<213> ORGANISM: Oryza sativa
<220> FEATURE:
<221> NAME/KEY: UNSURE
<222> LOCATION: (6)
<223> OTHER INFORMATION: Xaa = ANY AMINO ACID
<220> FEATURE:
<221> NAME/KEY: UNSURE
<222> LOCATION: (10)
<223> OTHER INFORMATION: Xaa = ANY AMINO ACID
<220> FEATURE:
<221> NAME/KEY: UNSURE
<222> LOCATION: (16)
<223> OTHER INFORMATION: Xaa = ANY AMINO ACID
<220> FEATURE:
<221> NAME/KEY: UNSURE
<222> LOCATION: (72)..(73)
<223> OTHER INFORMATION: Xaa = ANY AMINO ACID
<220> FEATURE:
<221> NAME/KEY: UNSURE
<222> LOCATION: (77)
<223> OTHER INFORMATION: Xaa = ANY AMINO ACID
<220> FEATURE:
<221> NAME/KEY: UNSURE
<222> LOCATION: (94)
<223> OTHER INFORMATION: Xaa = ANY AMINO ACID
<220> FEATURE:
<221> NAME/KEY: UNSURE
<222> LOCATION: (104)
<223> OTHER INFORMATION: Xaa = ANY AMINO ACID

<400> SEQUENCE: 16

Leu Lys Val Val Ser Xaa Thr Lys Phe Xaa Pro Gly Phe Leu Asn Xaa
 1               5                  10                  15

Gln Ile Ile Ile Leu Leu Ser Ser Leu Asn Val Pro Asp Ser Ile Phe
                20                  25                  30

Trp Gln Met Gln Glu Thr Met Leu Ser Asn Leu Asn Asn Ile Leu Ser
            35                  40                  45

Asp Arg Asp Val Ala Phe Glu Val Leu Thr Thr Ser Cys Ala Asp Asp
        50                  55                  60

Gly Asn Thr Ala Ala Leu Met Xaa Xaa Ala Gly Phe Xaa Pro Arg Thr
65                  70                  75                  80
```

```
Glu Pro His Leu Lys Ala Met Leu Leu Ala Ile Arg Ser Xaa Ala Gln
                85                  90                  95

Leu Gln Asp Leu Phe Glu Lys Xaa Arg Ile Phe Val Pro Asn Gly
            100                 105                 110

<210> SEQ ID NO 17
<211> LENGTH: 510
<212> TYPE: DNA
<213> ORGANISM: Glycine max
<220> FEATURE:
<221> NAME/KEY: unsure
<222> LOCATION: (509)
<223> OTHER INFORMATION: n=a,c,g or t

<400> SEQUENCE: 17
gagggttagt gagtgttgtt gacttcacat tgacgatcct ttttttttcc tgtctgtttg      60
cttccaattt ctcataccct caatcttcaa tcttggattg gagaacagca ttgattgagt     120
tttaccacac gatcgtagag cttctgatat ttttcgaaga ggaaaggcaa aagagttagc     180
atttaggatg ggaaaaacaa ttgagttgta tggattccct acatctgtga atgtgtctga     240
tgtaaagaca tttgtagagc agtatactgg tgaaggaact gtgttcgcca ttaaattaag     300
acatggaaaa ggtcgggttc caagagcatt tgcaattatt caattcacca ccgcaaattc     360
tgctacatct atgatgtcca gagctaacaa cattttgaga acattgcggt atgggacctc     420
ctatttaaaa gctcgggaaa tggaaagaga tattgtgcca aggccaaggg tgttttttgca    480 tagtttggat gatgtgaaac tgtcctttng                                      510

<210> SEQ ID NO 18
<211> LENGTH: 90
<212> TYPE: PRT
<213> ORGANISM: Glycine max

<400> SEQUENCE: 18

Met Gly Lys Thr Ile Glu Leu Tyr Gly Phe Pro Thr Ser Val Asn Val
  1               5                  10                  15

Ser Asp Val Lys Thr Phe Val Glu Gln Tyr Thr Gly Glu Gly Thr Val
             20                  25                  30

Phe Ala Ile Lys Leu Arg His Gly Lys Gly Arg Val Pro Arg Ala Phe
         35                  40                  45

Ala Ile Ile Gln Phe Thr Thr Ala Asn Ser Ala Thr Ser Met Met Ser
     50                  55                  60

Arg Ala Asn Asn Ile Leu Arg Thr Leu Arg Tyr Gly Thr Ser Tyr Leu
 65                  70                  75                  80

Lys Ala Arg Glu Met Glu Arg Asp Ile Val
                 85                  90

<210> SEQ ID NO 19
<211> LENGTH: 349
<212> TYPE: DNA
<213> ORGANISM: Glycine max
<220> FEATURE:
<221> NAME/KEY: unsure
<222> LOCATION: (60)
<223> OTHER INFORMATION: n=a,c,g or t
<220> FEATURE:
<221> NAME/KEY: unsure
<222> LOCATION: (120)
<223> OTHER INFORMATION: n=a,c,g or t
<220> FEATURE:
<221> NAME/KEY: unsure
<222> LOCATION: (286)
```

```
<223> OTHER INFORMATION: n=a,c,g or t
<220> FEATURE:
<221> NAME/KEY: unsure
<222> LOCATION: (299)
<223> OTHER INFORMATION: n=a,c,g or t
<220> FEATURE:
<221> NAME/KEY: unsure
<222> LOCATION: (307)
<223> OTHER INFORMATION: n=a,c,g or t
<220> FEATURE:
<221> NAME/KEY: unsure
<222> LOCATION: (344)
<223> OTHER INFORMATION: n=a,c,g or t

<400> SEQUENCE: 19
agtcaatgtg ttaagcttgc aaggttgttt tcaacagcaa ttgactttcc taaaactggn      60
gttccagctg ttatacctcc tgaacttatg tcaaagaata tcctgacttc atggagaagn     120
ctgacaaacc cacatacaaa tcgcataacg tgataggaaa gctctttagg gaagtggaaa     180
gaaatatcaa caaagtgccg gggcaattac atccttcaca aaattggttg cgagaagact    240
ccttacgacc aagaaattgg aaattggatg gcttcacggg attatnttgg atggatgcnt    300
tctatcncaa aaaccaattt tggactacaa agtttgggga aatnctgga               349

<210> SEQ ID NO 20
<211> LENGTH: 60
<212> TYPE: PRT
<213> ORGANISM: Glycine max
<220> FEATURE:
<221> NAME/KEY: UNSURE
<222> LOCATION: (41)
<223> OTHER INFORMATION: Xaa = ANY AMINO ACID

<400> SEQUENCE: 20

Ser Gln Cys Val Lys Leu Ala Arg Leu Phe Ser Thr Ala Ile Asp Phe
 1               5                  10                  15

Pro Lys Thr Gly Val Pro Ala Val Ile Pro Pro Glu Leu Tyr Val Lys
            20                  25                  30

Glu Tyr Pro Asp Phe Met Glu Lys Xaa Asp Lys Pro Thr Tyr Lys Ser
        35                  40                  45

His Asn Val Ile Gly Lys Leu Phe Arg Glu Val Glu
    50                  55                  60
```

PLANT RNA-DIRECTED RNA POLYMERASE PROTEINS

This application claims the benefit of U.S. Provisional Application No. 60/128,094, filed Apr. 7, 1999.

FIELD OF THE INVENTION

This invention is in the field of plant molecular biology. More specifically, this invention pertains to nucleic acid fragments encoding RNA-directed RNA polymerase proteins in plants and seeds.

BACKGROUND OF THE INVENTION

The phloem of a plant is a vascular tissue that is responsible for distributing the products of photosynthesis, nutrients and hormones to plant tissues and organs. Associated with the phloem are sieve elements and companion cells. Mature sieve cells are enucleate and must rely on physically connected companion cells (via a branched plasmodesmata) to provide many physiological functions. Sieve cells and companion cells together serve to deliver proteins into the phloem. Research has shown that specific mRNA molecules can be found in the plasmodesmata suggesting that there are mechanisms that participate in mRNA transport through the sieve cell-companion cell plasmodesmata connection (Xoconostle-Cazares, B., et al., (1999) *Science* 283:94–98). Some plant viruses have been shown to be able to establish systemic infections via movement proteins (MP) that have the capacity to interact with the plasmodemata and foster the cell—cell transport of MP and viral nucleic acids. Thus plant viruses have evolved the capacity to utilize existing plant pathways to traffic macromolecules to surrounding cells. Plants appear to have proteins similar to viral movement proteins that function in the transport of nucleic acids from cell to cell. Several plant genes that encode viral movement protein homologs have been identified in rice (elicitor-responsive gene 3, Os-FIERG1 and Os-FIERG2), one has been identified in corn (novel gene) and one has been identified in *Cucurbita maxima* (CmPP16) (Xoconostle-Cazares, B., et al., (1999) *Science* 283:94–98). Interestingly, movement of RNA throughout the plant is postulated by some to explain the phenomena of cosuppression. Thus, understanding plant viral movement protein homologs and how they work will provide mechanisms to control cosuppression and provide mechanisms to engineer plant virus resistance.

RNA-directed RNA polymerase (RdRP) is a plant-specific nucleic acid-synthesizing enzyme. Plants (tomato, chinese cabbage, cowpea, cauliflower, tobacco, and cucumber) are the only eukaryotes in which cellular RdRP has demonstrated Schiebel W., et al., (1998) *Plant Cell* 10:2087–2101) and furthermore, RdRP does not appear to be an RNA-dependent RNA polymerase, an enzyme that mediates viral RNA replication. The origin and biological function of the enzyme however is unknown. Studies on the antiviral state in transgenic plants suggest that RdRP could play a role in post-transcriptional gene silencing. Thus RdRP might play an important regulatory role in gene expression because it can transcribe RNA sequences (from RNA molecules) that could control the synthesis of nucleic acids and their translation into proteins. Understanding the function of RdRP in plants could provide a valuable tool to control gene expression via cosuppression and provide mechanisms to engineer plant virus resistance.

SUMMARY OF THE INVENTION

The present invention concerns an isolated polynucleotide comprising a nucleotide sequence selected from the group consisting of: (a) a first nucleotide sequence encoding a polypeptide of at least 157 amino acids having at least 80% identity based on the Clustal method of alignment when compared to a polypeptide selected from the group consisting of SEQ ID NOs:2, 4, 6, 8, 10 and 12 or (b) a second nucleotide sequence comprising the complement of the first nucleotide sequence.

In a second embodiment, it is preferred that the isolated polynucleotide of the claimed invention comprises a first nucleotide sequence which comprises a nucleic acid sequence selected from the group consisting of SEQ ID NOs:1, 3, 5, 7, 9 and 11 that codes for the polypeptide selected from the group consisting of SEQ ID NOs:2, 4, 6, 8, 10 and 12.

In a third embodiment, this invention concerns an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9 and 11 and the complement of such nucleotide sequences.

In a fourth embodiment, this invention relates to a chimeric gene comprising an isolated polynucleotide of the present invention operably linked to at least one suitable regulatory sequence.

In a fifth embodiment, the present invention concerns a host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

In a sixth embodiment, the invention also relates to a process for producing a host cell comprising a chimeric gene of the present invention or an isolated polynucleotide of the present invention, the process comprising either transforming or transfecting a compatible host cell with a chimeric gene or isolated polynucleotide of the present invention.

In a seventh embodiment, the invention concerns a RNA-directed RNA polymerase polypeptide of at least 157 amino acids comprising at least 80% identity based on the Clustal method of alignment compared to a polypeptide selected from the group consisting of SEQ ID NOs:2, 4, 6, 8, 10 and 12.

In an eighth embodiment, the invention relates to a method of selecting an isolated polynucleotide that affects the level of expression of a RNA-directed RNA polymerase polypeptide or enzyme activity in a host cell, preferably a plant cell, the method comprising the steps of: (a) constructing an isolated polynucleotide of the present invention or a chimeric gene of the present invention; (b) introducing the isolated polynucleotide or the chimeric gene into a host cell; (c) measuring the level of the RNA-directed RNA polymerase polypeptide or enzyme activity in the host cell containing the isolated polynucleotide; and (d) comparing the level of the RNA-directed RNA polymerase polypeptide or enzyme activity in the host cell containing the isolated polynucleotide with the level of the RNA-directed RNA polymerase polypeptide or enzyme activity in the host cell that does not contain the isolated polynucleotide.

In a ninth embodiment, the invention concerns a method of obtaining a nucleic acid fragment encoding a substantial portion of a RNA-directed RNA polymerase polypeptide, preferably a plant RNA-directed RNA polymerase polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs: 1, 3, 5, 7, 9 and 11 and the complement of such nucleotide sequences; and amplifying a nucleic acid fragment (preferably a cDNA inserted in a cloning vector) using the oligonucleotide primer. The amplified nucleic acid fragment preferably will encode a portion of a RNA-directed RNA polymerase amino acid sequence.

In a tenth embodiment, this invention relates to a method of obtaining a nucleic acid fragment encoding all or a substantial portion of the amino acid sequence encoding a RNA-directed RNA polymerase polypeptide comprising the steps of: probing a cDNA or genomic library with an isolated polynucleotide of the present invention: identifying a DNA clone that hybridizes with an isolated polynucleotide of the present invention; isolating the identified DNA clone; and sequencing the cDNA or genomic fragment that comprises the isolated DNA clone.

In an eleventh embodiment, this invention concerns a composition, such as a hybridization mixture, comprising an isolated polynucleotide or a polypeptide of the present invention.

In a twelfth embodiment, this invention concerns a method for positive selection of a transformed cell comprising: (a) transforming a host cell with the chimeric gene of the present invention or a construct of the present invention; and (b) growing the transformed host cell, preferably a plant cell, such as a monocot or a dicot, under conditions which allow expression of the RNA-directed RNA polymerase polynucleotide in an amount sufficient to complement a null mutant to provide a positive selection means.

BRIEF DESCRIPTION OF THE SEQUENCE LISTINGS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"). Nucleotide sequences, SEQ ID NOs:7, 9 and 11 and amino acid sequences SEQ ID NOs:8, 10 and 12 were determined by further sequence analysis of cDNA clones encoding the amino acid sequences set forth in SEQ ID NOs:14, 16, 18 and 20. Nucleotide SEQ ID NOs:13, 15, 17 and 19 and amino acid SEQ ID NOs:14, 16, 18 and 20 were among those disclosed in a U.S. Provisional Application No. 60/128,094, filed Apr. 7, 1999.

The sequence descriptions and Sequence Listing attached hereto comply with the rules governing nucleotide and/or amino acid sequence disclosures in patent applications as set forth in 37 C.F.R. §1.821–1.825.

TABLE 1

RNA-Directed RNA Polymerase Proteins

| | | SEQ ID NO: | |
|---|---|---|---|
| Protein | Clone Designation | (Nucleotide) | (Amino Acid) |
| RNA Directed RNA Polymerase | cho1c.pk006.o1 (EST) | 1 | 2 |
| RNA Directed RNA Polymerase | Contig Composed of: cpc1c.pk005.14 (EST) cpj1c.pk002.f24 (EST) p0005.cbmev75r (EST) p0031.ccmad44r (EST) p0049.curau90r (EST) | 3 | 4 |
| RNA Directed RNA Polymerase | p0016.ctsbo73r (EST) | 5 | 6 |
| RNA Directed RNA Polymerase | p0128.cpidb20r (FIS) | 7 | 8 |
| RNA Directed RNA Polymerase | rs11n.pk014.o23 (FIS) | 9 | 10 |
| RNA Directed RNA Polymerase | Contig composed of: sdp2c.pk007.121 (FIS) sdp2c.pk029.f24 (FIS) sdp3c.pk022.g17 (FIS) | 11 | 12 |
| RNA Directed RNA Polymerase | Contig Composed of: p0085.cscao73r (EST) p0086.cbsan57r (EST) p0099.ctbah82r (EST) p0107.cbca133r (EST) p0128.cpiax70r (EST) p0128.cpidd23r (EST) p0128.cpidb20r (EST) | 13 | 14 |
| RNA Directed RNA Polymerase | rs11n.pk014.o23 (EST) | 15 | 16 |
| RNA Directed RNA Polymerase | sdp2c.pk007.121 (EST) | 17 | 18 |
| RNA Directed RNA Polymerase | sdp3c.pk022.g17 (EST) | 19 | 20 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucieotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides derived from SEQ ID NOs: 1, 3, 5, 7, 9 and 11 or the complement of such sequences.

The term "isolated polynucleotide" refers to a polynucleotide that is substantially free from other nucleic acid sequences, such as and not limited to other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but does not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9 and 11 and the complement of such nucleotide sequences may be used in methods of selecting an isolated polynucleotide that affects the expression of a RNA-directed RNA polymerase polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or a chimeric gene of the present invention; introducing the isolated polynucleotide or the chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA—DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc. Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refers to nucleotide sequences located downstream of a coding sequence and includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. "Expression" may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers to a host cell which either lacks the expression of a certain polypeptide or expresses a polypeptide which is inactive or does not have any detectable expected enzymatic function.

"Mature protein" refers to a post-translationally processed polypeptide; i.e., one from which any pre- or propeptides present in the primary translation product have been removed. "Precursor protein" refers to the primary product of translation of mRNA; i.e., with pre- and propeptides still present. Pre- and propeptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol* 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence selected from the group consisting of: (a) a first nucleotide sequence encoding a polypeptide of at least 157 amino acids having at least 80% identity based on the Clustal method of alignment when compared to a polypeptide selected from the group consisting of SEQ ID NOs:2, 4, 6, 8, 10 and 12, or (b) a second nucleotide sequence comprising the complement of the first nucleotide sequence.

Preferably, the first nucleotide sequence comprises a nucleic acid sequence selected from the group consisting of SEQ ID NOs:1, 3, 5, 7, 9 and 11, that codes for the polypeptide selected from the group consisting of SEQ ID NOs:2, 4, 6, 8, 10 and 12.

Nucleic acid fragments encoding at least a portion of several RNA-directed RNA polymerase proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other RNA-directed RNA polymerase proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequence(s) can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9 and 11 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a RNA-directed RNA polymerase polypeptide, preferably a substantial portion of a plant RNA-directed RNA polymerase polypeptide, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9 and 11, and the complement of such nucleotide sequences; and amplifying a nucleic acid fragment (preferably a cDNA inserted in a cloning vector) using the oligonucleotide primer. The amplified nucleic acid fragment preferably will encode a portion of a RNA-directed RNA polymerase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of RNA-directed RNA polymerase activity in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a polypeptide of at least 157 amino acids that has at least 80% identity based on the Clustal method of alignment when compared to a polypeptide selected from the group consisting of SEQ ID NOs:2, 4, 6, 8, 10 and 12.

The instant polypeptides (or portions thereof) may be produced in heterologous host cells, particularly in the cells of microbial hosts, and can be used to prepare antibodies to the proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded RNA-directed RNA polymerase protein. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet*. 7:149–154). Although current methods of FISH mapping favor use of large clones (several to several hundred KB; see Laan et al. (1995) Genome Res. 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Nail. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries: Isolation and Sequencing of cDNA Clones cDNA libraries representing mRNAs from various corn, rice and soybean tissues were prepared. The characteristics of the libraries are described below.

TABLE 2 cDNA Libraries from Corn, Rice and Soybean

| Library | Tissue | Clone |
|---------|--------|-------|
| cho1c | Corn Embryo 20 Days After Pollination | cho1c.pk006.o1 |
| cpc1c | Corn pooled BMS treated with chemicals related to cGMP** | cpc1c.pk005.14 |
| cpj1c | Corn Pooled BMS Treated With Chemicals Related to Membrane Ionic Force*** | cpj1c.pk002.f24 |
| p0005 | Corn Immature Ear | p0005.cbmev75r |
| p0016 | Corn Tassel Shoots, Pooled, 0.1–1.4 cm | p0016.ctsbo73r |
| p0031 | Corn Shoot Culture | p0031.ccmad44r |
| p0049 | Corn Whole Kernels 5 Days After Pollination | p0049.curau90r |
| p0128 | Corn Primary and Secondary Immature Ear | p0128.cpidb20r |
| rsl1n | Rice 15-Day-Old Seedling* | rsl1n.pk014.o23 |
| sdp2c | Soybean Developing Pods (6–7 mm) | sdp2c.pk007.121 sdp2c.pk029.f24 |
| sdp3c | Soybean Developing Pods (8–9 mm) | sdp3c.pk022.g17 |

*This library was normalized essentially as described in U.S. Pat. No. 5,482,845, incorporated herein by reference.
**Chemicals used included suramin, MAS7, dipyryridamole, zaprinast, 8-bromo cGMPtrequinsin HCl, compound 48/80
***Chemicals used included valinomycin, bafilomycin A1, oligomycin, ionomycin cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding RNA-directed RNA polymerase proteins were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDna Clones Encoding RNA-Directed RNA Polymerase

The BLASTX search using the EST sequences from clones listed in Table 3 revealed similarity of the polypeptides encoded by the cDNAs to RNA-directed RNA polymerase from *Arabidopsis thaliana* (NCBI Identifier No. gi 3600048), *Arabidopsis thaliana* (NCBI Identifier No. gi 3687225), *Arabidopsis thaliana* (NCBI Identifier No. gi 6553930) and *Nicotiana tabacum* (NCBI Identifier No. gi 4138282). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 3

BLAST Results for Sequences Encoding
Polypeptides Homologous to *Arabidopsis thaliana* and
*Nicotiana tabacum* RNA-Directed RNA Polymerase

| Clone | Status | BLAST pLog Score |
| --- | --- | --- |
| cho1c.pk006.o1 | EST | 34.70 (gi 3687225) |
| Contig Composed of: cpc1c.pk005.14 (EST) | Contig | 169.00 (gi 3600048) |

TABLE 3-continued

BLAST Results for Sequences Encoding
Polypeptides Homologous to *Arabidopsis thaliana* and
*Nicotiana tabacum* RNA-Directed RNA Polymerase

| Clone | Status | BLAST pLog Score |
| --- | --- | --- |
| cpj1c.pk002.f24 (EST) | | |
| p0005.cbmev75r (EST) | | |
| p0031.ccmad44r (EST) | | |
| p0049.curau90r (EST) | | |
| p0016.ctsbo73r | CGS | >254.00 (gi 4138282) |
| p0128.cpidb20r | CGS | >254.00 (gi 6553930) |
| rsl1n.pk014.o23 | FIS | >254.00 (gi 6553930) |
| Contig composed of: sdp2c.pk007.121 (FIS) sdp2c.pk029.f24 (FIS) sdp3c.pk022.g17 (FIS) | CGS | >254.00 (gi 4138282) |

The data in Table 4 represents a calculation of the percent identity of the amino acid sequences set forth in SEQ ID NOs:2, 4, 6, 8, 10 and 12 and the *Arabidopsis thaliana* and *Nicotiana tabacum* sequences.

TABLE 4

Percent Identity of Amino Acid Sequences Deduced From the
Nucleotide Sequences of cDNA Clones Encoding
Polypeptides Homologous to *Arabidopsis thaliana* and
*Nicotiana tabacum* RNA-Directed RNA Polymerase

| SEQ ID NO. | Percent Identity to |
| --- | --- |
| 2 | 46% (gi 3687225) |
| 4 | 58% (gi 3600048) |
| 6 | 53% (gi 4138282) |
| 8 | 53% (gi 6553930) |
| 10 | 61% (gi 6553930) |
| 12 | 59% (gi 4138282) |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments, BLAST scores and probabilities indicate that the nucleic acid fragments comprising the instant cDNA clones encode a substantial portion of a RNA-directed RNA polymerase.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al., (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific construct composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin construct includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire construct is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed construct.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al. (1983)Gene 25:179–188) and the 3' region of the nopaline synthase gene from the T-DNA of the Ti plasmid of Agrobacterium tumefaciens. The seed construct comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/mL ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 mm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having RNA-directed RNA polymerase activity, wherein the amino acid sequence of the polypeptide and the amino acid sequence of SEQ ID NO:6 have at least 95% sequence identity, based on the Clustal alignment method with pairwise alignment default parameters of KTUPLE=1, GAP PENALTY=3, WINDOW=5 and DIAGONALS SAVED=5, or
   (b) the full-length complement of the nucleotide sequence of (a), wherein the complement and the nucleotide sequence of (a) have 100% complementarity.

2. The polynucleotide of claim 1, wherein the amino acid sequence of the polypeptide comprises the amino acid sequence SEQ ID NO:6.

3. The polynucleotide of claim 1 wherein the nucleotide sequence comprises the nucleotide sequence of SEQ ID NO:5.

4. A vector comprising the polynucleotide of claim 1.

5. A recombinant DNA construct comprising the polynucleotide of claim 1 operably linked to at least one regulatory sequence.

6. A method for transforming a cell, comprising transforming a cell with the polynucleotide of claim 1.

7. A cell comprising the recombinant DNA construct of claim 5.

8. A plant comprising the recombinant DNA construct of claim 5.

9. A seed comprising the recombinant DNA construct of claim 5.

* * * * *